US009101667B2

(12) United States Patent
Raja et al.

(10) Patent No.: US 9,101,667 B2
(45) Date of Patent: Aug. 11, 2015

(54) IONIC SILICONE HYDROGELS COMPRISING PHARMACEUTICAL AND/OR NEUTICEUTICAL COMPONENTS AND HAVING IMPROVED HYDROLYTIC STABILITY

(71) Applicant: Johnson & Johnson Vision Care, Inc., Jacksonville, FL (US)

(72) Inventors: Ranganath Raja, Jacksonville, FL (US); Sharmila Muthukrishnan, Chennai Tamil Nadu (IN); C. Surendran, The Nilgris Tamil Nadu (IN); R. Sridharan, Chennai Tamil Nadu (IN); Shivkumar Mahadevan, Orange Park, FL (US); Thomas L. Maggio, Jacksonville, FL (US); Azaam Alli, Jacksonville, FL (US); Scott L. Joslin, Ponte Vedra Beach, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 14/335,111

(22) Filed: Jul. 18, 2014

(65) Prior Publication Data

US 2014/0329859 A1 Nov. 6, 2014

Related U.S. Application Data

(60) Division of application No. 13/829,498, filed on Mar. 14, 2013, now abandoned, which is a continuation-in-part of application No. 12/567,352, filed on Sep. 25, 2009, now Pat. No. 8,470,906.

(60) Provisional application No. 61/101,455, filed on Sep. 30, 2008.

(51) Int. Cl.
*G02B 1/04* (2006.01)
*A61K 47/34* (2006.01)
*C08F 290/06* (2006.01)

(52) U.S. Cl.
CPC ............ *A61K 47/34* (2013.01); *C08F 290/068* (2013.01); *G02B 1/043* (2013.01)

(58) Field of Classification Search
None
See application file for complete search history.

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | |
| 4,113,224 A | 9/1978 | Clark et al. | |
| 4,182,802 A | 1/1980 | Loshaek et al. | |
| 4,197,266 A | 4/1980 | Clark et al. | |
| 4,260,725 A | 4/1981 | Keogh et al. | |
| 4,276,402 A | 6/1981 | Chromecek et al. | |
| 4,277,595 A | 7/1981 | Deichert et al. | |
| 4,769,431 A | 9/1988 | Ratkowski | |
| 4,810,764 A | 3/1989 | Friends et al. | |
| 4,910,277 A | 3/1990 | Bambury et al. | |
| 5,070,215 A | 12/1991 | Bambury et al. | |
| 5,244,981 A | 9/1993 | Seidner et al. | |
| 5,260,000 A | 11/1993 | Nandu et al. | |
| 5,314,960 A | 5/1994 | Spinelli et al. | |
| 5,321,108 A | 6/1994 | Kunzler et al. | |
| 5,331,067 A | 7/1994 | Seidner et al. | |
| 5,352,714 A | 10/1994 | Lai et al. | |
| 5,371,147 A | 12/1994 | Spinelli et al. | |
| 5,387,662 A | 2/1995 | Kunzler et al. | |
| 5,451,617 A | 9/1995 | Lai et al. | |
| 5,539,016 A | 7/1996 | Kunzler et al. | |
| 5,760,100 A | 6/1998 | Nicolson et al. | |
| 5,944,853 A | 8/1999 | Molock et al. | |
| 6,020,445 A | 2/2000 | Vanderlaan et al. | |
| 6,197,842 B1 | 3/2001 | Marchin et al. | |
| 6,367,929 B1 | 4/2002 | Maiden et al. | |
| 6,634,748 B1 | 10/2003 | Vanderlaan et al. | |
| 6,822,016 B2 | 11/2004 | McCabe et al. | |
| 6,867,245 B2 | 3/2005 | Iwata et al. | |
| 6,943,203 B2 | 9/2005 | Vanderlaan et al. | |
| 7,052,131 B2 | 5/2006 | McCabe et al. | |
| 7,879,267 B2 | 2/2011 | Turner et al. | |
| 7,923,482 B2 | 4/2011 | Matsuzawa et al. | |
| 2002/0016383 A1 | 2/2002 | Iwata et al. | |
| 2002/0107324 A1 | 8/2002 | Vanderlaan et al. | |
| 2003/0052424 A1 | 3/2003 | Turner et al. | |
| 2003/0125498 A1 | 7/2003 | McCabe et al. | |
| 2003/0162862 A1 | 8/2003 | McCabe et al. | |

(Continued)

FOREIGN PATENT DOCUMENTS

| | | |
|---|---|---|
| EA | 5340 B1 | 2/2005 |
| JP | 2000501853 | 2/2000 |

(Continued)

OTHER PUBLICATIONS

Crivello, et al, Photoinitiators for Free Radical Cationic & Anionic Photopolymerisation, 2nd Edition, vol. III, pp. 275-298, John Wiley and Sons, New York, 1998.

Maissa, Cecile. "Influence of Contact Lens Material Surface Characteristics and Replacement Frequency on Protein and Lipid Deposition." Optometry and Vision Science. 75.9 (1998): 697-704.

PCT International Search Report, dated Feb. 2, 2010, for PCT Int'l Appln. No. PCT/US2009/058605.

Salton, M.R.J. "The Properties of Lysozyme and its Action on Microorganisms." Bacteriological Review. 21.2 (1957): 82-100.

*Primary Examiner* — Marc Zimmer
(74) *Attorney, Agent, or Firm* — Karen A. Harding

(57) ABSTRACT

The present invention relates to ionic silicone hydrogel polymers displaying improved thermal stability. More specifically, the present invention relates to a polymer formed from reactive components comprising at least one silicone component and at least one ionic component comprising at least one anionic group. The polymers of the present invention display good thermal stability and desirable protein uptake.

29 Claims, 6 Drawing Sheets

(56) References Cited

U.S. PATENT DOCUMENTS

| | | |
|---|---|---|
| 2005/0258408 A1 | 11/2005 | Molock et al. |
| 2006/0276608 A1 | 12/2006 | Lang et al. |
| 2007/0149428 A1 | 6/2007 | Ammon et al. |
| 2008/0081850 A1 | 4/2008 | Fujisawa et al. |
| 2008/0081894 A1 | 4/2008 | Fujisawa et al. |
| 2008/0102095 A1 | 5/2008 | Young et al. |
| 2008/0151236 A1 | 6/2008 | Prince et al. |
| 2008/0273168 A1* | 11/2008 | Rathore et al. ............ 351/160 H |
| 2009/0176905 A1 | 7/2009 | Matsuzawa et al. |
| 2010/0130711 A1 | 5/2010 | Chu et al. |
| 2010/0249356 A1* | 9/2010 | Rathore et al. .................. 528/26 |
| 2010/0280146 A1 | 11/2010 | Vanderlaan et al. |
| 2011/0111001 A1* | 5/2011 | Young et al. ............... 424/409 |
| 2011/0134387 A1 | 6/2011 | Samuel et al. |
| 2012/0088861 A1 | 4/2012 | Huang et al. |
| 2012/0327504 A1 | 12/2012 | Kayashima et al. |

FOREIGN PATENT DOCUMENTS

| | | |
|---|---|---|
| KR | 2004011566 A | 2/2004 |
| TW | 200819819 | 5/2008 |
| WO | 9631792 A1 | 10/1996 |
| WO | 9722019 A1 | 6/1997 |
| WO | 0055212 A1 | 9/2000 |
| WO | 03022321 A2 | 3/2003 |
| WO | 03022322 A2 | 3/2003 |
| WO | 2008005147 A2 | 1/2008 |
| WO | 2008042158 A1 | 4/2008 |
| WO | 2008055048 A2 | 5/2008 |
| WO | 2008061992 A2 | 5/2008 |
| WO | 2008116131 A2 | 9/2008 |

* cited by examiner

IONIC SILICONE HYDROGELS COMPRISING PHARMACEUTICAL AND/OR NEUTICEUTICAL COMPONENTS AND HAVING IMPROVED HYDROLYTIC STABILITY

RELATED APPLICATIONS

This application is a division of U.S. application Ser. No. 13/829,498, filed Mar. 14, 2013; which is a continuation-in-part of U.S. application Ser. No. 12/567,352, filed Sep. 25, 2009, now U.S. Pat. No. 8,470,906 issued Jun. 25, 2013, which claims the benefit of Provisional Patent Application U.S. Ser. No. 61/101,455, filed on Sep. 30, 2008, the contents of which are relied upon and incorporated by reference.

FIELD OF THE INVENTION

The present invention relates to ionic silicone hydrogels, and ophthalmic devices formed therefrom, which display desirable protein uptake profiles, improved hydrolytic stability and desirable drug uptake.

BACKGROUND OF THE INVENTION

It is well known that contact lenses can be used to improve vision. Various contact lenses have been commercially produced for many years. Hydrogel contact lenses are very popular today. These lenses are formed from hydrophilic polymers and copolymers containing repeating units from hydroxyethylmethylacrylate (HEMA). Of these contact lenses formed from copolymers of HEMA and methacrylic acid, are among the most comfortable, and have the lowest rate of adverse events. Contact lenses formed from copolymers of HEMA and MAA, such ACUVUE contact lenses, display substantial amounts of lysozyme uptake (greater than 500 μg) and retain a majority of the uptaken proteins in their native state. However, hydrogel contact lenses generally have oxygen permeabilities that are less than about 30.

Contact lenses made from silicone hydrogels have been disclosed. These silicone hydrogel lenses have oxygen permeabilities greater than about 60, and many provide reduced levels of hypoxia compared to conventional hydrogel contact lenses. However, silicone hydrogel lenses have different rates for adverse events than conventional hydrogels, and it would be desirable to maintain the oxygen transmissibility of a silicone hydrogel, but achieve the low adverse event rate of the best conventional hydrogel lenses. Unfortunately, attempts to add anionic components to silicone hydrogels in the past have produced contact lenses which are not hydrolytically stable and display moduli which increase when exposed to water and heat. For example, the modulus of Purevision lenses (Bausch & Lomb) increase from 155 psi to 576 psi when heated at 95° C. for one week. It is believed that the cause of this increase in modulus is the hydrolysis of terminal siloxane groups followed by condensation reactions to form new siloxane bonds and introduce new crosslinks. Even though Purevision lenses contain about 1 weight % ionicity, they uptake relatively low lysozyme levels (less than about 50 μg), and a majority of the protein uptaken is denatured.

It has been suggested that the instability of ionic silicone hydrogels could be reduced by using silicones components having bulky alkyl or aryl groups instead of silicone monomers such as 3-methacryloxypropyltris(trimethylsiloxy)silane ("TRIS") or 2-methyl-,2-hydroxy-3-[3-[1,3,3,3-tetramethyl-1-[(trimethylsilyl)oxy]disiloxanyl]propoxy]propyl ester ("SiGMA"). However, the bulky siloxane monomers are not commercially available and may be expensive to make.

SUMMARY OF THE INVENTION

The present invention relates to ionic silicone hydrogel polymers displaying improved thermal stability and desirable protein uptake. More specifically, the present invention relates to silicone hydrogel polymers and contact lenses formed from reactive components comprising at least one silicone component and at least one anionic component in an amount between about 0.1 and 0.8 wt %.

The present invention relates to ionic silicone hydrogel polymers displaying improved thermal stability and desirable protein uptake. More specifically, the present invention relates to silicone hydrogel polymer and contact lenses formed from reactive components comprising at least one silicone component and at least one anionic component comprising at least one carboxylic acid group in an amount between about 0.1 and about 10 mmol/gm.

DETAILED DESCRIPTION

Figure 1:
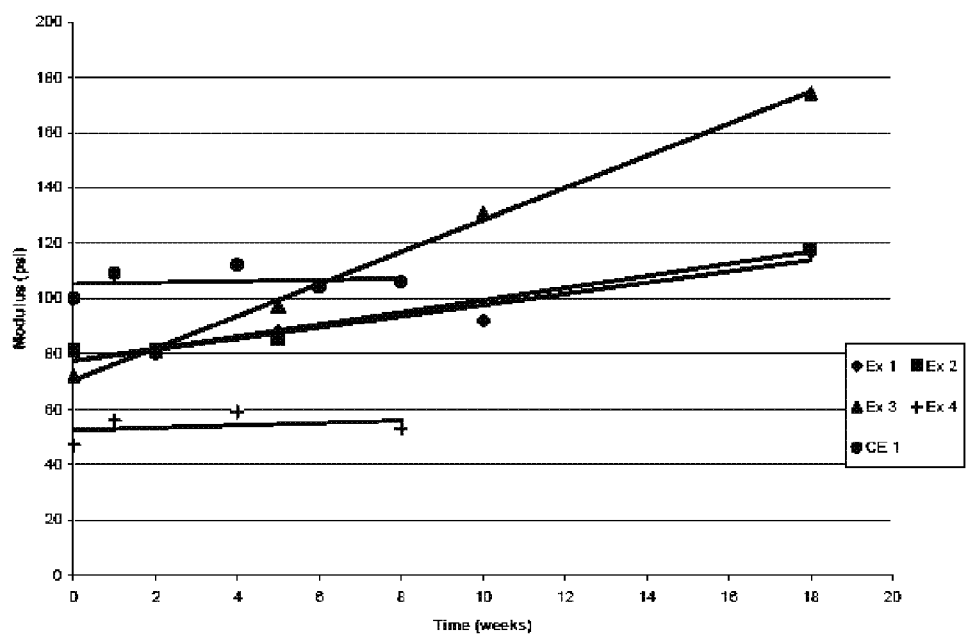
FIG. 1 is a graph showing the change in modulus at 55° C. of the lenses of Examples 1-4 and Comparative Example 1 as a function of time.
Figure 2:
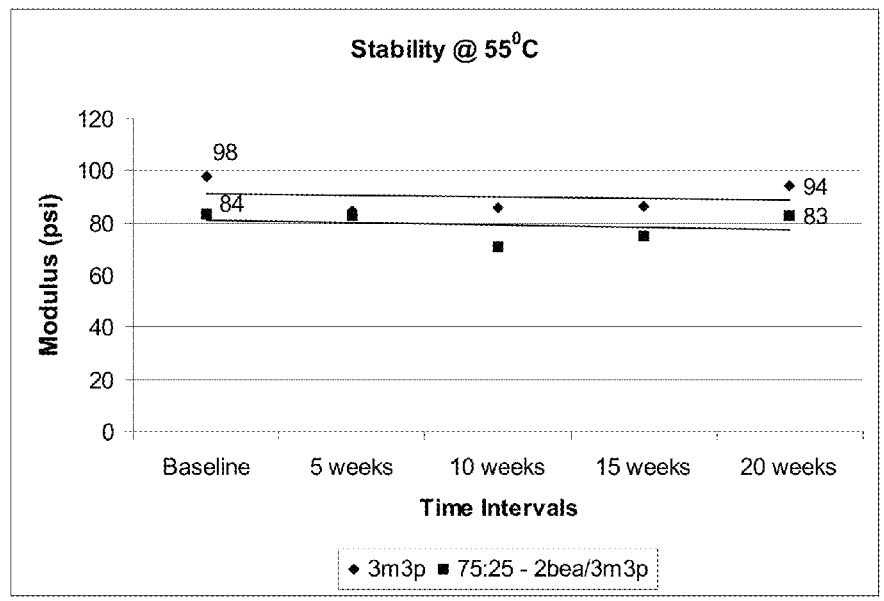
FIGS. 2-4 are graphs showing, for the lenses of Examples 6-7, the change in modulus, toughness and elongation at 55° C. as a function of time.

It has been surprisingly found that ionic silicone hydrogel polymers and articles made therefrom may be made having acceptable thermal stability and desirable protein uptake characteristics.

As used herein, a "biomedical device" is any article that is designed to be used while either in or on mammalian tissues or fluid. Examples of these devices include but are not limited to catheters, implants, stents, and ophthalmic devices such as intraocular lenses and contact lenses.

As used herein an "ophthalmic device" is any device which resides in or on the eye or any part of the eye, including the cornea, eyelids and ocular glands. These devices can provide optical correction, cosmetic enhancement, vision enhancement, therapeutic benefit (for example as bandages) or delivery of active components such as pharmaceutical and neutraceutical components, or a combination of any of the foregoing. Examples of ophthalmic devices include lenses and optical and ocular inserts, including, but not limited to punctal plugs and the like.

As used herein, the term "lens" refers to ophthalmic devices that reside in or on the eye. The term lens includes but is not limited to soft contact lenses, hard contact lenses, intraocular lenses, overlay lenses.

The medical devices, ophthalmic devices and lenses of the present invention are made from silicone elastomers or hydrogels, which include but are not limited to silicone hydrogels, and silicone-fluorohydrogels. These hydrogels contain hydrophobic and hydrophilic monomers that are covalently bound to one another in the cured lens. As used herein "uptake" means associated in, with or on the lens, deposited in or on the lens.

As used herein "reactive mixture" refers to the mixture of components (both reactive and non-reactive) which are mixed together and subjected to polymerization conditions to form the ionic silicone hydrogels of the present invention. The reactive mixture comprises reactive components such as monomers, macromers, prepolymers; cross-linkers, initiators, diluents and additives such as wetting agents, release agents, dyes, light absorbing compounds such as UV absorbers and photochromic compounds, any of which may be reactive or non-reactive but are capable of being retained within the resulting medical device, as well as pharmaceutical and neutriceutical compounds. It will be appreciated that a wide range of additives may be added based upon the medical device which is made, and its intended use. Concentrations of components of the reactive mixture are given in weight % of all components in the reaction mixture, excluding diluent. When diluents are used their concentrations are given as weight % based upon the amount of all components in the reaction mixture and the diluent.

Anionic components are components comprising at least one anionic group and at least one reactive group. Anionic groups are groups which bear a negative charge. Examples of anionic groups include carboxylate groups, phosphates, sulfates, sulfonates, phosphonates, borates, mixtures thereof and the like. In one embodiment the anionic groups comprise three to ten carbon atoms, and in another, three to eight carbon atoms. In an embodiment the anionic groups comprise carboxylic acid groups.

Reactive groups include groups that can undergo free radical and/or cationic polymerization under polymerization conditions. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl (meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. In one embodiment the reactive groups comprises (meth)acrylate, acryloxy, (meth)acrylamide, and mixtures thereof.

Any chemical name preceded by (meth), for example (meth)acrylate, includes both the unsubstituted and methyl substituted compound.

Examples of suitable anionic components include reactive carboxylic acids, including alkylacryl acids, such as (meth) acrylic acid, acrylic acid, itaconic acid, crotonic acid, cinnamic acid, vinylbenzoic acid, fumaric acid, maleic acid, monoesters of furmaric acid, maelic acid and itaconic acid; N-vinyloxycarbonyl alanine (VINAL), reactive sulfonate salts, including sodium-2-(acrylamido)-2-methylpropane sulphonate, 3-sulphopropyl (meth)acrylate potassium salt, 3-sulphopropyl (meth)acrylate sodium salt, bis 3-sulphopropyl itaconate di sodium, bis 3-sulphopropyl itaconate di potassium, vinyl sulphonate sodium salt, vinyl sulphonate salt, styrene sulfonate, sulfoethyl methacrylate and mixtures thereof and the like. In one embodiment the anionic component is selected from reactive carboxylic acids, in another from methacrylic acid and N-vinyloxycarbonyl alanine. In one embodiment the ionic component comprises methacrylic acid.

In one embodiment, the anionic components is included in the reactive mixture in amounts between about 0.05 and about 2 weight % and in some embodiments between about 0.1 and about 0.8 weight %. In one embodiment, the anionic components is included in the reactive mixture in amounts between about 0.05 and about 5 mol %.

In another embodiment, the anionic component comprises at least one carboxylic acid group and is present in the reactive mixture in amounts between about 10 mmol/100 g and about 20 mmol/100 g. By maintaining the concentration of anioinic component within the ranges recited herein with the specified silicone components, the stability of the polymer may be improved, and uptake of certain cationic pharmaceutical compounds is increased. Surprisingly, it has also been found that polymers having the amounts of anionic component recited herein have desirable protein uptake profiles in addition to improved stability.

The silicone hydrogel polymers of the present invention display stable modulus. As used herein, stable modulus are those which increase less than about 30%, and in some embodiments less than about 20% over eight weeks, at 55° C. In some embodiments the silicone hydrogel polymers of the present invention display modulus that increase by less than about 20% over 20 weeks at 55° C. The ionic silicone hydrogel polymers of the present invention also display stable modulus. In other embodiments the ionic silicone hydrogel lenses of the present invention display stable modulii which increase less than about 30%, and in some embodiments less than about 20% over three autoclave cycles (20 minutes at 121° C.). In some embodiments the silicone hydrogel polymers of the present invention display modulus that increase by less than about 20% over 20 weeks over three autoclave cycles. In another embodiment, the ionic silicone hydrogels of the present invention display modulii which change less than about 30%, about 20% or even less than about 10% over 12 or 18 months at 25° C. and ambient humidity.

Silicone components are reactive and non-reactive components which comprise at least one "—Si—O—Si—" group. It is preferred that silicone and its attached oxygen account for about 10 weight percent of said silicone component, more preferably more than about 20 weight percent.

Prior attempts to add anionic components to silicone hydrogels have generally resulted in polymers which display modulii which increase over time or when exposed to heat. It is believed that the cause of the increasing modulus is the hydrolysis of terminal siloxane groups followed by condensation reactions to form new siloxane bonds and introduce new crosslinks. Hydrolytic stability of silicone groups (specifically the silicon-oxygen bond) is believed to be influenced by the substituents on the Si atom. Bulkier groups provide greater hydrolytic stability through increased steric hindrance. The substituents can be alkyl groups (methyl, ethyl, propyl, butyl etc.), aryl (e.g. benzyl) or even other silicon-containing groups. On the basis of steric hindrance, silicone materials containing trimethylsilyl (—OSiMe$_3$) groups (such as SiMAA or TRIS) are generally less hydrolytically stable in the presence of ionic components than compounds containing polydimethylsiloxane [(—OSiMe$_2$)$_n$] chains, such as mPDMS. Thus, in this embodiment, the stability of the polymer is further improved by selection of the silicone containing components in combination with controlling the concentration of the anionic component.

In one embodiment, the silicone component comprises, consists or consists essentially of at least one polydimethylsiloxane chain, and in another embodiment, comprise less than 5 wt % components comprising at least one TMS group and in another embodiment all silicone components are free of TMS groups. In another embodiment the silicone components comprise less than 5 wt % TRIS, and in another embodiment, are free of TRIS. Still further, the reactive mixtures of the present invention are free of linear polysiloxane crosslinkers.

In yet another embodiment the silicone components comprise, consists or consists essentially only one reactive group and at least one polydimethylsiloxane chain. In another embodiment the reactive mixture is free of multifunctional silicone component which comprise polyalkylsiloxane groups, and particularly polydimethylsiloxane chains in the backbone of the molecule (multifunctional, linear polydialkylsiloxanes). Silicone hydrogels comprising multifunctional, linear polydialkylsiloxanes, such as linear polydimethylsiloxane crosslinkers have been disclosed to be thermalytically unstable.

Silicone-containing components which contain no TMS groups include those disclosed in WO2008/0412158, and reactive PDMS components of Formula I:

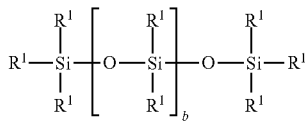

wherein b is 2 to 20, 3 to 15 or in some embodiments 3 to 10; at least one terminal $R^1$ comprises a monovalent reactive group, the other terminal $R^1$ comprises a monovalent reactive group or a monovalent alkyl group having 1 to 16 carbon atoms, and the remaining $R^1$ are selected from monovalent alkyl groups having 1 to 16 carbon atoms, and in another embodiment from monovalent alkyl groups having 1 to 6 carbon atoms. In yet another embodiment, b is 3 to 15, one terminal $R^1$ comprises a monovalent reactive group, for example, a (meth)acryloxy $C_{1-6}$ alkyl, which may be further substituted with at least one hydrophilic group, such as hydroxyl, ether or a combination thereof, the other terminal $R^1$ comprises a monovalent alkyl group having 1 to 6 carbon atoms and the remaining $R^1$ comprise monovalent alkyl group having 1 to 3 carbon atoms. In one embodiment one terminal $R^1$ is (meth)acryloxy $C_{1-6}$ alkyl, which is optionally substituted with ether or hydroxyl, the other terminal $R^1$ is a $C_{1-4}$ alkyl, and the remaining $R^1$ are methyl or ethyl. Non-limiting examples of PDMS components of this embodiment include (mono-(2-hydroxy-3-methacryloxypropyl)-propyl ether terminated polydimethylsiloxane (400-1000 MW)) ("HO-mPDMS"), and monomethacryloxypropyl terminated mono-n-$C_{1-4}$ alkyl terminated polydimethylsiloxanes, including monomethacryloxypropyl terminated mono-n-butyl terminated polydimethylsiloxanes (800-1000 MW), ("mPDMS") and monomethacryloxypropyl terminated methyl terminated polydimethylsiloxanes (800-1000 MW), ("mPDMS"). In one embodiment all silicone in the reactive mixture are PDMS components.

In another embodiment, the multifunctional silicone components which are excluded from the reactive mixtures comprise those where b is 5 to 400 or from 10 to 300, both terminal $R^1$ comprise monovalent reactive groups and the remaining $R^1$ are independently selected from monovalent alkyl groups having 1 to 18 carbon atoms which may have ether linkages between carbon atoms and may further comprise halogen.

In another embodiment, one $R^1$ comprises a vinyl carbonate or carbamate of the formula:

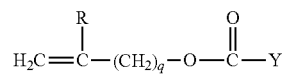

wherein: Y denotes O—, S— or NH—;
R denotes, hydrogen or methyl; q is 1, 2, 3 or 4; and b is 1-50. In these embodiments care must be taken to make sure the vinyl carbonate or carbamate silicone component does not also comprising TMS groups.

Suitable silicone-containing vinyl carbonate or vinyl carbamate monomers specifically include: 1,3-bis[4-(vinyloxycarbonyloxy)but-1-yl]tetramethyl-disiloxane; and

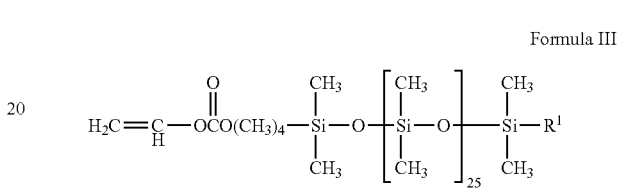

wherein $R^1$ is as defined for a non-reactive terminal group above.

Where biomedical devices with modulus below about 200 are desired, only one $R^1$ shall comprise a monovalent reactive group.

In one embodiment, where a silicone hydrogel lens is desired, the lens of the present invention will be made from a reactive mixture comprising at least about 20 weight % and in some embodiments between about 20 and 70% wt silicone-containing components based on total weight of reactive monomer components from which the polymer is made.

Another class of silicone-containing components includes polyurethane macromers of the following formulae:

$$(*D*A*D*G)_a*D*D*E^1;\qquad\text{Formulae IV-VI}$$

wherein:
D denotes an alkyl diradical, an alkyl cycloalkyl diradical, a cycloalkyl diradical, an aryl diradical or an alkylaryl diradical having 6 to 30 carbon atoms,
G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;
* denotes a urethane or ureido linkage;
$a$ is at least 1;
A denotes a divalent polymeric radical of formula:

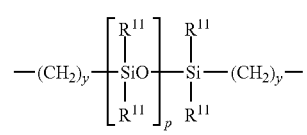

$R^{11}$ independently denotes an alkyl or fluoro-substituted alkyl group having 1 to 10 carbon atoms which may contain ether linkages between carbon atoms; y is at least 1; and p provides a moiety weight of 400 to 10,000; $E^1$ independently denotes a polymerizable unsaturated organic radical represented by formula:

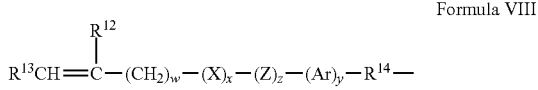

Formula VIII wherein: $R^{12}$ is hydrogen or methyl; $R^{13}$ is hydrogen, an alkyl radical having 1 to 6 carbon atoms, or a —CO—Y—$R^{15}$ radical wherein Y is —O—, —S— or —NH—; $R^{14}$ is a divalent radical having 1 to 12 carbon atoms; X denotes —CO— or —OCO—; Z denotes —O— or —NH—; Ar denotes an aromatic radical having 6 to 30 carbon atoms; w is 0 to 6; x is 0 or 1; y is 0 or 1; and z is 0 or 1.

In one embodiment of the present invention, a modulus of less than about 120 psi is desired. In this embodiment, to insure the desired balance of oxygen transmissibility and modulus it is preferred that all components having more than one polymerizable functional group ("multifunctional components") make up no more than 10 mmol/100 g of the reactive components, and preferably no more than 7 mmol/100 g of the reactive components.

The silicone containing components may be present in amounts up to about 95 weight %, and in some embodiments between about 10 and about 80 and in other embodiments between about 20 and about 70 weight %, based upon all reactive components.

The reactive mixture may also comprise at least one hydrophilic component in addition to the ionic component. Hydrophilic monomers can be any of the hydrophilic monomers known to be useful to make hydrogels.

One class of suitable hydrophilic monomers include acrylic- or vinyl-containing monomers. Such hydrophilic monomers may themselves be used as crosslinking agents, however, where hydrophilic monomers having more than one polymerizable functional group are used, their concentration should be limited as discussed above to provide a contact lens having the desired modulus. The term "vinyl-type" or "vinyl-containing" monomers refer to monomers containing the vinyl grouping (—CH=$CH_2$) and are generally highly reactive. Such hydrophilic vinyl-containing monomers are known to polymerize relatively easily.

"Acrylic-type" or "acrylic-containing" monomers are those monomers containing the acrylic group: ($CH_2$=CRCOX) wherein R is H or $CH_3$, and X is O or N, which are also known to polymerize readily, such as N,N-dimethyl acrylamide (DMA), 2-hydroxyethyl methacrylate (HEMA), glycerol methacrylate, 2-hydroxyethyl methacrylamide, polyethyleneglycol monomethacrylate, mixtures thereof and the like.

Hydrophilic vinyl-containing monomers which may be incorporated into the silicone hydrogels of the present invention include monomers such as N-vinyl amides, N-vinyl lactams (e.g. NVP), N-vinyl-N-methyl acetamide, N-vinyl-N-ethyl acetamide, N-vinyl-N-ethyl formamide, N-vinyl formamide, with NVP being preferred.

Other hydrophilic monomers that can be employed in the invention include polyoxyethylene polyols having one or more of the terminal hydroxyl groups replaced with a functional group containing a polymerizable double bond. Examples include polyethylene glycol, ethoxylated alkyl glucoside, and ethoxylated bisphenol A reacted with one or more molar equivalents of an end-capping group such as isocyanatoethyl methacrylate ("IEM"), methacrylic anhydride, methacryloyl chloride, vinylbenzoyl chloride, or the like, to produce a polyethylene polyol having one or more terminal polymerizable olefinic groups bonded to the polyethylene polyol through linking moieties such as carbamate or ester groups.

Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art.

In one embodiment the hydrophilic comprises at least one hydrophilic monomer such as DMA, HEMA, glycerol methacrylate, 2-hydroxyethyl methacrylamide, NVP, N-vinyl-N-methyl acrylamide, polyethyleneglycol monomethacrylate, and combinations thereof. In another embodiment, the hydrophilic monomers comprise at least one of DMA, HEMA, NVP and N-vinyl-N-methyl acrylamide and mixtures thereof. In another embodiment, the hydrophilic monomer comprises DMA.

The hydrophilic monomers may be present in a wide range of amounts, depending upon the specific balance of properties desired. Amounts of hydrophilic monomer up to about 50 and preferably between about 5 and about 50 weight %, based upon all reactive components are acceptable. For example, in one embodiment lenses of the present invention comprise a water content of at least about 25%, and in another embodiment between about 30 and about 70%. For these embodiments, the hydrophilic monomer may be included in amounts between about 20 and about 50 weight %.

Other components that can be present in the reaction mixture used to form the contact lenses of this invention include wetting agents, such as those disclosed in U.S. Pat. No. 6,367,929, WO03/22321, WO03/22322, compatibilizing components, such as those disclosed in US2003/162,862 and US2003/2003/125,498, ultra-violet absorbing compounds, medicinal agents, antimicrobial compounds, copolymerizable and nonpolymerizable dyes, release agents, reactive tints, pigments, combinations thereof and the like. The sum of additional components may be up to about 20 wt %. In one embodiment the reaction mixtures comprise up to about 18 wt % wetting agent, and in another embodiment, between about 5 and about 18 wt % wetting agent.

A polymerization catalyst may be included in the reaction mixture. The polymerization initiators includes compounds such as lauryl peroxide, benzoyl peroxide, isopropyl percarbonate, azobisisobutyronitrile, and the like, that generate free radicals at moderately elevated temperatures, and photoinitiator systems such as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ester and a combination of camphorquinone and ethyl 4-(N,N-dimethylamino)benzoate. Commercially available visible light initiator systems include Irgacure 819, Irgacure 1700, Irgacure 1800, Irgacure 819, Irgacure 1850 (all from Ciba Specialty Chemicals) and Lucirin TPO initiator (available from BASF). Commercially available UV photoinitiators include Darocur 1173 and Darocur 2959 (Ciba Specialty Chemicals). These and other photoinitiators which may be used are disclosed in Volume III, Photoinitiators for Free Radical Cationic & Anionic Photopolymerization, $2^{nd}$ Edition by J. V. Crivello & K. Dietliker; edited by G. Bradley; John Wiley and Sons; New York; 1998.

The initiator is used in the reaction mixture in effective amounts to initiate photopolymerization of the reaction mixture, e.g., from about 0.1 to about 2 parts by weight per 100 parts of reactive monomer. Polymerization of the reaction mixture can be initiated using the appropriate choice of heat or visible or ultraviolet light or other means depending on the polymerization initiator used. Alternatively, initiation can be conducted without a photoinitiator using, for example, e-beam. However, when a photoinitiator is used, the preferred initiators are bisacylphosphine oxides, such as bis(2,4,6-trimethylbenzoyl)-phenyl phosphine oxide (Irgacure 819®) or a combination of 1-hydroxycyclohexyl phenyl ketone and bis(2,6-dimethoxybenzoyl)-2,4-4-trimethylpentyl phosphine oxide (DMBAPO), and in another embodiment the method of polymerization initiation is via visible light activation. A preferred initiator is bis(2,4,6-trimethylbenzoyl)-phenyl phosphine oxide (Irgacure 819®).

The reactive components (silicone containing component, hydrophilic monomers, wetting agents, and other components which are reacted to form the lens) are mixed together either with or without a diluent to form the reaction mixture.

In one embodiment a diluent is used having a polarity sufficiently low to solubilize the non-polar components in the reactive mixture at reaction conditions. One way to characterize the polarity of the diluents of the present invention is via the Hansen solubility parameter, δp. In certain embodiments, the δp is less than about 10, and preferably less than about 6. Suitable diluents are further disclosed in U.S. Ser. No. 60/452,898 and U.S. Pat. No. 6,020,445.

Classes of suitable diluents include, without limitation, alcohols having 2 to 20 carbons, amides having 10 to 20 carbon atoms derived from primary amines, ethers, polyethers, ketones having 3 to 10 carbon atoms, and carboxylic acids having 8 to 20 carbon atoms. For all solvents, as the number of carbons increase, the number of polar moieties may also be increased to provide the desired level of water miscibility. In some embodiments, primary and tertiary alcohols are preferred. Preferred classes include alcohols having 4 to 20 carbons and carboxylic acids having 10 to 20 carbon atoms.

In one embodiment the diluents are selected from 1,2-octanediol, t-amyl alcohol, 3-methyl-3-pentanol, decanoic acid, 3,7-dimethyl-3-octanol, tripropylene methyl ether (TPME), butoxy ethyl acetate, mixtures thereof and the like.

In one embodiment the diluents are selected from diluents that have some degree of solubility in water. In some embodiments at least about three percent of the diluent is miscible water. Examples of water soluble diluents include 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, decanoic acid, octanoic acid, dodecanoic acid, 1-ethoxy-2-propanol, 1-tert-butoxy-2-propanol, EH-5 (commercially available from Ethox Chemicals), 2,3, 6,7-tetrahydroxy-2,3,6,7-tetramethyl octane, 9-(1-methylethyl)-2,5,8,10,13,16-hexaoxaheptadecane, 3,5,7,9,11,13-hexamethoxy-1-tetradecanol, mixtures thereof and the like.

The reactive mixture of the present invention may be cured via any known process for molding the reaction mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. In one embodiment, the contact lenses of this invention are formed by the direct molding of the silicone hydrogels, which is economical, and enables precise control over the final shape of the hydrated lens. For this method, the reaction mixture is placed in a mold having the shape of the final desired silicone hydrogel, i.e. water-swollen polymer, and the reaction mixture is subjected to conditions whereby the monomers polymerize, to thereby produce a polymer in the approximate shape of the final desired product.

After curing the lens is subjected to extraction to remove unreacted components and release the lens from the lens mold. The extraction may be done using conventional extraction fluids, such organic solvents, such as alcohols or may be extracted using aqueous solutions.

Aqueous solutions are solutions which comprise water. In one embodiment the aqueous solutions of the present invention comprise at least about 30% water, in some embodiments at least about 50% water, in some embodiments at least about 70% water and in others at least about 90 weight % water. Aqueous solutions may also include additional water soluble components such as release agents, wetting agents, slip agents, pharmaceutical and nutraceutical components, combinations thereof and the like.

The lense of the present invention display surprisingly efficient uptake of cationic drugs compared to uncharged silicone hydrogel lenses and to anionic conventional lenses, such as etafilcon A. The uptake drug/[ionic component], may be calculated using the following equation:

$$[(\text{drug uptake}_{ionic\ lens}/\text{drug uptake}_{non\text{-}ionic\ lens})/[\text{ionic component}]_{ionic\ lens}]\times 100$$

Lenses of the present invention display drug uptake/[ionic component] of greater than 100, greater than about 200, and in some embodiments greater than about 250. Because the lenses of the present invention are more efficient at uptaking the selected cationic compound, less concentrated loading solutions may be used.

Suitable pharmaceutical and nutraceutical components are known and include cationic drugs and neutriceuticals. Examples include those for the treatment of dry eye mitigation and/or prevention (including contact lens related dry eye, excessive tear evaporation and Non-Sjogren's aqueous tear deficiency), glaucoma, allergies (including antihistimines and mast cell inhibitors), ocular inflammation, ocular redness, ocular itching, bacterial, viral and fungal infections, prevention or slowing of myopia progression, and anaesthetics. Examples of cationic drugs include atropine, pirenzepine, doxycycline, brimonidine, brinzolamide, dorzolamide, betaxolol, apraclonidine, ccr2 antagonist, olopatadine, alcaftadine, betaxolol, bupivacaine, carbachol, carteolol, chlortetracycline, cyclopentolate, dibutoline, dipivefrin, ephedrine, erythromycin, gentamycin, gramicidin, homatropine ketotifen, levobunolol, levocabastine, lidocaine, lignocaine, lomefloxacin, mepivacaine, naphazoline, neomycin, ofloxacin, oxybuprocaine, pheniramine, physostigmine, pilocarpine, polymyxin B, proparacaine, pyrilamine, tetracaine, tetracycline, tetrahydozoline, timolol, tropicamide, vidarabine, pharmaceutically acceptable salts thereof and combinations thereof and the like. In another embodiment suitable pharmaceutical components include atropine, pirenzepine, doxycycline, brimonidine, brinzolamide, dorzolamide, betaxolol, apraclonidine, ccr2 antagonist, olopatadine, alcaftadine, betaxolol, bupivacaine, carbachol, carteolol, chlortetracycline, cyclopentolate, dibutoline, dipivefrin, erythromycin, gentamycin, gramicidin, homatropine ketotifen, levobunolol, levocabastine, lidocaine, lignocaine, lomefloxacin, mepivacaine, naphazoline, ofloxacin, pheniramine, physostigmine, pilocarpine, polymyxin B, proparacaine, pyrilamine, tetracaine, tetrahydozoline, timolol, tropicamide pharmaceutically acceptable salts thereof and combinations thereof and the like.

In another embodiment the cationic drugs include atropine, ketotifen, olopatadine, alcaftadine, levocabastine, pirenzepine, doxycycline, brimonidine, brinzolamide, dorzolamide, betaxolol, apraclonidine, ccr2 antagonist, olopatadine pharmaceutically acceptable salts thereof and combinations thereof and the like.

The drugs may be incorporated into the lenses in a symptom mitigating effective amount. Suitable amounts will vary for each drug, but include those between about the weight of the drug contained in an ophthalmic device prior to its use by a patient wherein such minimum effective amount alleviates the symptoms of the condition being treated. The minimum effective amount may vary depending upon the efficacy of a particular drug. General ranges include between about 5 µg and about less than 200 µg, and in some embodiments between about 9 µg and about less than 100 µg, with the symptom mitigating effective amount being selected to achieve the desired clinical result while minimizing undesired side effects.

For example, if the anti-allergic agent is ketotifen fumarate, the minimum effective amount is between greater than about 9 µg and about less than 90 µg, more particularly between about 40 µg and greater than about 9 µg, most preferably about 20 µg.

It is preferred that the minimum effective amount of drug alleviates the symptoms for between about 5 minutes, and about 24 hours from insertion of the ophthalmic device into the eye of a user, more preferably between about 5 minutes and about 16 hours, most preferably between about 5 minutes and about 12 hours.

The lenses of the present invention display surprisingly improved drug uptake compared to uncharged silicone hydrogel lenses and to anionic conventional lenses, such as etafilcon A. This is illustrated by the increase in uptake efficiency, uptake/[MAA], which was calculated using the following equation:

$$[(\text{Ketotifen uptake}_{ionic\ lens}/\text{Ketotifen uptake}_{non-ionic\ lens})/[\text{MAA}]_{ionic\ lens}] \times 100$$

So, for Example 20 (59.1/18.4)/1=320.

Thus in one embodiment the lenses of the present invention display uptake efficiencies greater than about 200, greater than about 250, and in some embodiments, greater than about 300.

Still further the invention includes a method of making an ophthalmic device comprising about a minimum effective amount of an anti-allergic agent comprising the step of treating an ophthalmic device with a solution comprising said anti-allergic agent, wherein the amount of said anti-allergic agent in said solution exceeds the minimum effective amount. It is preferred that the minimum effective amount is exceeded by between about 1.0% and about 1000%, in a volume of solution that is between about 500 µL and about 5000 µL preferably between about 50% and about 500%, in a volume of solution that is between about 500 µL and about 3000 µL most preferably about 50% in a volume of solution that is about 1000 µL.

As used herein treating means physical methods of contacting the solution containing an anti-allergic agent and the ophthalmic device. Preferably treating refers to physical methods of contacting the anti-allergic agent with the ophthalmic devices prior to selling or otherwise delivering the ophthalmic devices to a patient. The ophthalmic devices may be treated with the anti-allergic agent anytime after they are polymerized.

Release agents are compounds or mixtures of compounds which, when combined with water, decrease the time required to release a contact lens from a mold, as compared to the time required to release such a lens using an aqueous solution that does not comprise the release agent. In one embodiment the aqueous solutions comprise less than about 10 weight %, and in others less than about 5 weight % organic solvents such as isopropyl alcohol, and in another embodiment are free from organic solvents. In these embodiments the aqueous solutions do not require special handling, such as purification, recycling or special disposal procedures.

In various embodiments, extraction can be accomplished, for example, via immersion of the lens in an aqueous solution or exposing the lens to a flow of an aqueous solution. In various embodiments, extraction can also include, for example, one or more of: heating the aqueous solution; stirring the aqueous solution; increasing the level of release aid in the aqueous solution to a level sufficient to cause release of the lens; mechanical or ultrasonic agitation of the lens; and incorporating at least one leach aid in the aqueous solution to a level sufficient to facilitate adequate removal of unreacted components from the lens. The foregoing may be conducted in batch or continuous processes, with or without the addition of heat, agitation or both.

Some embodiments can also include the application of physical agitation to facilitate leach and release. For example, the lens mold part to which a lens is adhered, can be vibrated or caused to move back and forth within an aqueous solution. Other embodiments may include ultrasonic waves through the aqueous solution.

These and other similar processes can provide an acceptable means of releasing the lens.

As used herein, "released from a mold" means that a lens is either completely separated from the mold, or is only loosely attached so that it can be removed with mild agitation or pushed off with a swab. In the process of the present invention the conditions used include temperature less than 99° C. for less than about 1 hour.

The lenses may be sterilized by known means such as, but not limited to autoclaving.

In addition to displaying desirable stability, the lenses of the present invention also display compatibility with the components of human tears.

Human tears are complex and contain a mixture of proteins, lipids and other components which help to keep the eye lubricated. Examples of lipids classes include wax ester, cholesterolesters and cholesterol. Examples of proteins which are found in human tears include lactoferrin, lysozyme, lipocalin, serum albumin, secretory immunoglobulin A. Lipocalin is a lipid binding protein. The amount of lipocalin uptake to a contact lens has been negatively correlated to lens wettability (as measured via contact angle, such as via sessile drop), the propensity of lenses to uptake lipids from the tear film and consequently deposits on the front surface of the lens. Lenses which uptake low levels of lipocalin are therefore desirable. In one embodiment of the present invention, the lenses uptake less than about 3 µg lipocalin from a 2 mg/ml lipocalin solution over 72 hours incubation at 35° C.

Lysozyme is generally present in human tears in substantial concentrations. Lysozyme is bacteriolytic and believed to protect the eye against bacterial infection. The amount of lysozyme which associates with commercially available contact lenses varies greatly from only a few micrograms to over 800 micrograms for etafilcon A contact lenses (commercially available from Johnson & Johnson Vision Care, Inc., under the ACUVUE and ACUVUE2 brand names). Etafilcon A contact lenses have been commercially available for many years and display some of the lowest adverse event rates of any soft contact lens. Thus, contact lenses which uptake substantial levels of lysozyme are desirable. The lenses of the present invention uptake at least about 50 μg, 100 μg, 200 μg, 500 μg of lysozyme and in some embodiments at least about 800 μg lysozyme, all from a 2 mg/ml solution over 72 hours incubation at 35° C.

In addition to lysozyme, lactoferrin is another important cationic protein in the tears, mainly by the virtue of its antibacterial and anti-inflammatory properties. Upon wear, contact lenses uptake various amounts of lactoferrin, depending upon their polymer composition (for non-surface modified lenses) and the composition and integrity of the surface coating (for surface modified contact lenses). In one embodiment of the present invention, lenses uptake at least about 5 μg, and in some embodiments, at least about 10 micrograms lactoferrin following overnight soaking of the lenses in 2 mls of a 2 mg/ml lactoferrin solution. The lactoferrin solution contains lactoferrin from human milk (Sigma L-0520) solubilized at a concentration of 2 mg/ml in phosphate saline buffer, Lenses are incubated in 2 ml of the lactoferrin solution per lens for 72 hours at 35° C., using the procedure described below for lipocalin and lysozyme.

The form of the proteins in, on and associated with the lens is also important. Denatured proteins are believed to contribute to corneal inflammatory events and wearer discomfort. Environmental factors such as pH, ocular surface temperature, wear time and closed eye wear are believed to contribute to the denaturation of proteins. However, lenses of different compositions can display markedly different protein uptake and denaturation profiles. In one embodiment of the present invention, a majority of the proteins uptaken by the lenses of the present invention are and remain in the native form during wear. In other embodiments at least about 50%, at least about 70 and at least about 80% of uptaken proteins are and remain native after 24 hours, 3 days and during the intended wear period.

In one embodiment the ophthalmic devices of the present invention also uptake less than about 20%, in some embodiments less than about 10%, and in other embodiments less than about 5% Polyquaternium-1 (dimethyl-bis[(E)-4-[tris (2-hydroxyethyl)azaniumyl]but-2-enyl]azanium trichloride) ("PQ1") from an ophthalmic solution containing 0.001 wt % PQ1).

The lenses of the present invention have a number of desirable properties in addition to the protein uptake characteristics described herein. In one embodiment the lenses have an oxygen permeability greater than about 50 and in other embodiment greater than about 60, in other embodiments greater than about 80 and in still other embodiments at least about 100. In some embodiments the lenses have tensile moduli less than about 100 psi.

It will be appreciated that all of the tests specified herein have a certain amount of inherent test error. Accordingly, results reported herein are not to be taken as absolute numbers, but numerical ranges based upon the precision of the particular test.

Modulus (tensile modulus) is measured by using the crosshead of a constant rate of movement type tensile testing machine equipped with a load cell that is lowered to the initial gauge height. A suitable testing machine includes an Instron model 1122. A dog-bone shaped sample from a −1.00 power lens having a 0.522 inch length, 0.276 inch "ear" width and 0.213 inch "neck" width is loaded into the grips and elongated at a constant rate of strain of 2 in/min. until it breaks. The initial gauge length of the sample (Lo) and sample length at break (Lf) are measured. At least five specimens of each composition are measured and the average is reported. Tensile modulus is measured at the initial linear portion of the stress/strain curve.

Percent elongation is $=[(Lf-Lo)/Lo]\times 100$.

Diameter may be measured using the modulation image generated from a Mach-Zehnder interferometer with the lenses submersed in saline solution and mounted concave surface down in a cuvette, as further described in US2008/0151236. The lenses are equilibrated for 15 minutes at about 20° C. before measurement.

Water content is measured as follows. The lenses to be tested are allowed to sit in packing solution for 24 hours. Each of three test lens are removed from packing solution using a sponge tipped swab and placed on blotting wipes which have been dampened with packing solution. Both sides of the lens are contacted with the wipe. Using tweezers, the test lens are placed in a weighing pan and weighed. The two more sets of samples are prepared and weighed as above. The pan and lenses are weighed three times and the average is the wet weight.

The dry weight is measured by placing the sample pans in a vacuum oven which has been preheated to 60° C. for 30 minutes. Vacuum is applied until at least 0.4 inches Hg is attained. The vacuum valve and pump are turned off and the lenses are dried for four hours. The purge valve is opened and the oven is allowed reach atmospheric pressure. The pans are removed and weighed. The water content is calculated as follows:

$$\text{Wet weight} = \text{combined wet weight of pan and lenses} - \text{weight of weighing pan}$$

$$\text{Dry weight} = \text{combined dry weight of pan and lens} - \text{weight of weighing pan}$$

$$\%\text{ water content} = \frac{(\text{wet weight} - \text{dry weight})}{\text{wet weight}} \times 100$$

The average and standard deviation of the water content are calculated for the samples are reported.

Lysozyme and lipocalin uptake were measured out using the following solutions and method.

The lysozyme solution contained lysozyme from chicken egg white (Sigma, L7651) solubilized at a concentration of 2 mg/ml in phosphate saline buffer supplemented by Sodium bicarbonate at 1.37 g/l and D-Glucose at 0.1 g/l.

The lipocalin solution contained B Lactoglobulin (Lipocalin) from bovine milk (Sigma, L3908) solubilized at a concentration of 2 mg/ml in phosphate saline buffer supplemented by Sodium bicarbonate at 1.37 g/l and D-Glucose at 0.1 g/l.

Three lenses for each example were tested using each protein solution, and three were tested using PBS as a control solution. The test lenses were blotted on sterile gauze to remove packing solution and aseptically transferred, using sterile forceps, into sterile, 24 well cell culture plates (one lens per well) each well containing 2 ml of lysozyme solution. Each lens was fully immersed in the solution. 2 ml of the lysozyme solution was placed in a well without a contact lens as a control.

The plates containing the lenses and the control plates containing only protein solution and the lenses in the PBS, were parafilmed to prevent evaporation and dehydration, placed onto an orbital shaker and incubated at 35° C., with agitation at 100 rpm for 72 hours. After the 72 hour incubation period the lenses were rinsed 3 to 5 times by dipping lenses into three (3) separate vials containing approximately 200 ml volume of PBS. The lenses were blotted on a paper towel to remove excess PBS solution and transferred into sterile conical tubes (1 lens per tube), each tube containing a volume of PBS determined based upon an estimate of lysozyme uptake expected based upon on each lens composition. The lysozyme concentration in each tube to be tested needs to be within the albumin standards range as described by the manufacturer (0.05 micogram to 30 micrograms). Samples known to uptake a level of lysozyme lower than 100 µg per lens were diluted 5 times. Samples known to uptake levels of lysozyme higher than 500 µg per lens (such as etafilcon A lenses) are diluted 20 times.

1 ml aliquot of PBS was used for samples 9, CE2 and the balafilcon lenses, and 20 ml for etafilcon A lens. Each control lens was identically processed, except that the well plates contained PBS instead of either lysozyme or lipocalin solution.

Lysozyme and Lipocalin uptake was determined using on-lens bicinchoninic acid method using QP-BCA kit (Sigma, QP-BCA) following the procedure described by the manufacturer (the standards prep is described in the kit) and is calculated by subtracting the optical density measured on PBS soaked lenses (background) from the optical density determined on lenses soaked in lysozyme solution.

Optical density was measured using a SynergyII Microplate reader capable for reading optical density at 562 nm.

Lysozyme activity was measured using the solution and incubation procedure described above for lysozyme uptake.

After the incubation period the lenses were rinsed 3 to 5 times by dipping lenses into three (3) separate vials containing approximately 200 ml volume of PBS. The lenses were blotted on a paper towel to remove excess PBS solution and transferred into sterile, 24 well cell culture plates (one lens per well) each containing 2 ml of extraction solution composed of a 50:50 mix of 0.2% of trifluoroacetic acid and acetonitrile (TFA/ACN) solution. The lenses were incubated in the extraction solution for 16 hours at room temperature.

In parallel, the lysozyme control solution was diluted in the extraction buffer to a range of concentrations with bracket the expected lysozyme uptake of the lenses being analyzed. For the examples of the present application the expected lysozyme concentrations were 10, 50, 100, 800 and the control solution were diluted to those concentrations and incubated for 16 hours at room temperature. The lysozyme extracts from both the lenses and the controls were assayed for lysozyme activity using EnzChek® Lysozyme Assay Kit (invitrogen) following the instructions described by the manufacturer.

The EnzChek kit is a fluorescence based assay to measure levels of lysozyme activity in solution down to 20 U/ml. The test measures lysozyme activity on Micrococcus Lysodeikticus cell walls, which are labelled in such a degree that the fluorescence is quenched. Lysozyme action relieves this quenching, yielding an increase in fluorescence that is proportional to lysozyme activity. The fluorescence increase is measured using a fluorescence microplate reader that can detect fluorescein using excitation/emission weivelenghs of 494/518 nm. A Synergy HT microplate reader was used in the examples of the present application.

The assay is based on the preparation of lysozyme standard curve using the same lysozyme incubated with the lenses or as a control. Lysozyme activity is expressed in fluorescence units and plotted against lysozyme concentrations expressed in Units/ml. Activity of lysozyme extracted from the lenses as well as lysozyme control was measured and converted using standard curve to an activity expressed in units per ml.

The percentage of active or native lysozyme is determined by comparing lysozyme activity on lenses to that in the control solution and is calculated following the formula below:

% of active or native lysozyme on lens=Lysozyme (unit/ml) extracted from the lens×100/Lysozyme (unit per ml) obtained from control.

PQ1 uptake was measured as follows. The HPLC is calibrated using a series of standard PQ1 solutions prepared having the following concentrations: 2, 4, 6, 8, 12 and 15 µg/mL. Lenses were placed into polypropylene contact lens case with 3 mL of Optifree Replenish (which contains 0.001 wt % PQ1, and is commercially available from Alcon). A control lens case, containing 3 mL of solution, but no contact lens was also prepared. The lenses and control solutions were allowed to sit at room temperature for 72 hours. 1 ml of solution was removed from each of the samples and controls and mixed with trifluoroacetic acid (10 µL). The analysis was conducted using HPLC/ELSD and a Phenomenex Luna C4 (4.6 mm×5 mm; 5 µm particle size) column and the following conditions Instrument: Agilent 1200 HPLC or equivalent with Sedere Sedex 85 ELSD
Sedex 85 ELSD: T=60° C., Gain=10, Pressure=3.4 bar, Filter=1 s
Mobile Phase A: $H_2O$ (0.1% TFA)
Mobile Phase B: Acetonitrile (0.1% TFA)
Column Temperature: 40° C.
Injection Volume: 100 µL

TABLE I

| HPLC Conditions. | | | |
|---|---|---|---|
| Time (minutes) | % A | % B | Flow Rate (mL/min) |
| 0.00 | 100 | 0 | 1.2 |
| 1.00 | 100 | 0 | 1.2 |
| 5.00 | 5 | 100 | 1.2 |
| 8.50 | 5 | 100 | 1.2 |
| 8.60 | 100 | 0 | 1.2 |
| 11.00 | 100 | 0 | 1.2 |

Three lenses were run for each analysis, and the results were averaged.

Oxygen permeability (Dk) was determined by the polarographic method generally described in ISO 9913-1: 1996(E), but with the following variations. The measurement is conducted at an environment containing 2.1% oxygen. This environment is created by equipping the test chamber with nitrogen and air inputs set at the appropriate ratio, for example 1800 ml/min of nitrogen and 200 ml/min of air. The t/Dk is calculated using the adjusted oxygen concentration. Borate buffered saline was used. The dark current was measured by using a pure humidified nitrogen environment instead of applying MMA lenses. The lenses were not blotted before measuring. Four lenses were stacked instead of using lenses of varied thickness. A curved sensor was used in place of a flat sensor. The resulting Dk value is reported in barrers.

These examples do not limit the invention. They are meant only to suggest a method of practicing the invention. Those knowledgeable in contact lenses as well as other specialties may find other methods of practicing the invention. However, those methods are deemed to be within the scope of this invention.

EXAMPLES

The following abbreviations are used in the examples below:

Macromer Macromer prepared according to the procedure disclosed under Macromer Preparation in Example 1, of US-2003-0052424-A1 acPDMS bis-3-acryloxy-2-hydroxypropyloxypropyl polydimethylsiloxane (MW 2000, acrylated polydimethylsiloxane) from Degussa Blue HEMA the reaction product of Reactive Blue 4 and HEMA, as described in Example 4 of U.S. Pat. No. 5,944,853

CGI 819 bis(2,4,6-trimethylbenzoyl)-phenylphosphineoxide

CGI 1850 1:1 (wgt) blend of 1-hydroxycyclohexyl phenyl ketone and bis(2,6-dimethoxybenzoyl)-2,4-4-trimethylpentyl phosphine oxide D3O 3,7-dimethyl-3-octanol DMA N,N-dimethylacrylamide EGDMA ethyleneglycol dimethacrylate HEMA 2-hydroxyethyl methacrylate MAA methacrylic acid mPDMS monomethacryloxypropyl terminated mono-n-butyl terminated polydimethylsiloxane, manufactured by Gelest, molecular weight specified in the Examples Norbloc 2-(2'-hydroxy-5-methacrylyloxyethylphenyl)-2H-benzotriazole mPDMS-OH mono-(3-methacryloxy-2-hydroxypropyloxy) propyl terminated, mono-butyl terminated polydimethylsiloxane, made according to Example 8, molecular weight 612

PBS phosphate buffered saline, containing calcium and magnesium (Sigma, D8662).

PQ-1 Polyquaternium-1 (dimethyl-bis[(E)-4-[tris(2-hydroxyethyl)azaniumyl]but-2-enyl]azanium trichloride)

PVP poly(N-vinyl pyrrolidone) (K values noted)

SiGMA (3-methacryloxy-2-hydroxypropyloxy)propylbis (trimethylsiloxy)silane

TEGDMA tetraethyleneglycol dimethacrylate

TPME tripropylene methyl ether

Examples 1-3

Lenses having the formulations shown in Table 1 were made as follows. The diluent for Examples 1-3 was a mixture of 18.33 gm PVP 2500/48.34 gm t-amyl alcohol. The diluent for Example 4 was 16.2 gm PVP 2500/64.8 gm t-amyl alcohol. The monomer mixes were dispensed into Zeonor front and Zeonor:Polypropylene (55:45) back curves. The monomer mixtures were cured under visible light (Philips TL-03 bulbs) in a nitrogen atmosphere (about 3% $O_2$) using the following cure profile: 1 mW/cm² for about 20 seconds at ambient temperature, 1.8±0.5 mW/cm² for about 270 seconds at 75±5° C., and 6.0±0.5 mW/cm² for about 270 seconds at about 75±5° C.

After curing, the molds were opened, and the lenses released in 70% IPA in DI water. After about 40-50 minutes the lenses were transferred into: i) 70% IPA in DI water for about 40-50 minutes; ii) 70% IPA in DI water for about 40-50 minutes; and iii) DI water for at least about 30 minutes.

The lenses were packaged in 950+/−50 uL of borate buffered sodium sulfate solution with 50 ppm methyl cellulose (SSPS) using polypropylene bowls and foil, and autoclaved once (124° C., 18 minutes).

TABLE 1

| Component | Ex 1 | Ex 2 | Ex 3 | Ex 4 | CE 1 |
|---|---|---|---|---|---|
| Macromer | 0 | 0 | 0 | 6.93 | 0 |
| HO-mPDMS 1000 | 0 | 0 | 0 | 45.54 | 0 |
| SiGMA | 30 | 30 | 30 | 0 | 28 |
| acPDMS 2000 | 5 | 5 | 5 | 0 | 0 |
| mPDMS 1000 | 28 | 28 | 28 | 0 | 31 |
| DMA | 19 | 19 | 19 | 19.8 | 24 |
| HEMA | 7.75 | 8.25 | 7.15 | 12.41 | 6 |
| MAA | 1 | 0.5 | 1.6 | 1 | 0 |
| Norbloc | 2 | 2 | 2 | 2.18 | 2 |
| PVP 360,000 | 7 | 7 | 7 | 11.88 | 7 |
| Blue HEMA | 0.02 | 0.02 | 0.02 | 0.02 | 0.02 |
| CGI 819 | 0.23 | 0.23 | 0.23 | 0.25 | 0.25* |
| Sum of monomers | 100 | 100 | 100 | 100 | 100 |
| Diluent: | 40 | 40 | 40 | 44.75 | 23** |

*CGI 1850
**D3O

Example 4

Lenses were made using the formulation listed in Table 1, for Example 4, and the conditions described in Example 1, except that the cure profile was: 1 mW/cm² (10-30 seconds, ambient temperature), 1.5±0.2 mW/cm² (about 160 seconds, at 80±5° C.), 6.0±0.2 mW/cm² (about 320 seconds, at about 80±5° C.)].

The molds were opened, and the lenses released in 70% IPA in DI water. After 60 minutes the lenses were transferred into: i) 100% IPA for 60 minutes; ii) 70% IPA in DI water for 60 minutes; iii) DI water for 30 minutes; iv) DI water for 30 minutes; v) DI water for 30 minutes.

The lenses were silver-treated by exposure to aqueous sodium iodide solution, followed by exposure to aqueous silver nitrate solution. The lenses were packaged in 10 mL of SSPS in glass vials with silicone stoppers, and autoclaved three times (121° C., 30 minutes).

Stability Evaluation

Lenses from Examples 1-4 and Comparative Example 1 were placed in a chamber with temperature controlled at 55° C. Lenses were pulled from the chamber at established intervals, and tested for modulus, maximum strain and diameter (for Examples 1-3, lenses were pulled at each time point for measurement as follows: 8-10 lenses for diameter measurement, 9 lenses for % $H_2O$ and 8-10 lenses for mechanical property testing; for Example 4, 5 lenses were pulled at each time point as follows: 5 lenses for diameter testing, 9 lenses for % $H_2O$ and 5 lenses for mechanical properties). The stability data from Examples 1-4 is shown in FIG. 1. In addition, stability data from lenses made according to Comparative Example 1, below, which had no ionic component, are also included as a non-ionic control.

The modulus of the lenses was measured at various time intervals and is reported in Tables 2 and 3.

TABLE 2

| Ex # | Stability Product | [MAA] wt % | MAA | Time (wk) | Modulus (psi) | Elongation (%) | Diameter (mm) |
|---|---|---|---|---|---|---|---|
| 1 | 0.0017 | 1 | 0.012 | 0 | 81 + 7 | 252 + 47 | 13.66 + 0.06 |
| 1 | 0.0017 | 1 | 0.012 | 2 | 80 + 6 | 243 + 20 | 13.59 + 0.06 |
| 1 | 0.0017 | 1 | 0.012 | 5 | 88 + 6 | 163 + 28 | 13.59 + 0.14 |
| 1 | 0.0015 | 1 | 0.012 | 10 | 92 + 8 | 175 + 34 | 13.56 + 0.05 |
| 1 | 0.0017 | 1 | 0.012 | 18 | 117 + 11 | 112 + 34 | 13.54 + 0.1 |
| 2 | 0.0008 | 0.5 | 0.006 | 0 | 81 + 8 | 294 + 42 | 13.53 + 0.04 |
| 2 | 0.0008 | 0.5 | 0.006 | 2 | 81 + 5 | 284 + 41 | 13.59 + 0.05 |
| 2 | 0.0008 | 0.5 | 0.006 | 5 | 85 + 5 | 216 + 15 | 13.49 + 0.08 |
| 2 | 0.0008 | 0.5 | 0.006 | 10 | NM | NM | NM |
| 2 | 0.0008 | 0.5 | 0.006 | 18 | 118 + 8 | 144 + 20 | 13.49 + 0.12 |
| 3 | 0.0026 | 1.6 | 0.019 | 0 | 72 + 5 | 210 + 67 | 14.00 + 0.07 |
| 3 | 0.0026 | 1.6 | 0.019 | 2 | 81 + 6 | 169 + 37 | 13.94 + 0.05 |
| 3 | 0.0024 | 1.6 | 0.019 | 5 | 97 + 4 | 104 + 26 | 13.89 + 0.04 |
| 3 | 0.0026 | 1.6 | 0.019 | 10 | 131 + 7 | 81 + 15 | 13.72 + 0.06 |
| 3 | 0.0026 | 1.6 | 0.019 | 18 | 174 + 11 | 48 + 11 | 13.62 + 0.07 |

* Moles/100 gram of reactive components

TABLE 3

| Ex # | Stability Product | [MAA] wt % | MAA* | Time (wk) | Modulus (psi) | Elongation (%) | Diameter (mm) |
|---|---|---|---|---|---|---|---|
| 4 | 0.00019 | 1 | 0.012 | 0 | 47 + 8 | 73 + 51 | 13.89 + 0.04 |
| 4 | 0.00019 | 1 | 0.012 | 1 | 56 + 11 | 169 + 97 | 13.94 + 0.09 |
| 4 | 0.00019 | 1 | 0.012 | 4 | 59 + 15 | 106 + 56 | 13.92 + 0.05 |
| 4 | 0.00019 | 1 | 0.012 | 6 | NM | NM | NM |
| 4 | 0.00019 | 1 | 0.012 | 8 | 53 + 1 | 140 + 73 | 13.91 + 0.1 |
| CE1 | 0 | 0 | 0 | 0 | 100 + 5 | 247 + 45 | 14.05 + 0.02 |
| CE1 | 0 | 0 | 0 | 1 | 109 + 11 | 234 + 52 | 14.07 + 0.01 |
| CE1 | 0 | 0 | 0 | 4 | 112 + 3 | 220 + 52 | 14.05 + 0.02 |
| CE1 | 0 | 0 | 0 | 6 | 104 + 9 | 249 + 38 | 14.08 + 0.02 |
| CE1 | 0 | 0 | 0 | 8 | 106 + 16 | 202 + 61 | 14.05 + 0.01 |

*Moles/100 gram of reactive components

FIG. 1 is a graph showing of the modulus vs. time data included in Tables 2 and 3, above. The lines for the comparative Example and Example 4 are very flat, due to the small changes in modulus over the time periods measured. As the concentration of methacrylic acid and mole product increases, the slope of the line also increases, with a substantial increase between Example 1 (having a concentration of 1 wt % methacrylic acid and a stability product of 0.0017) and Example 3, having a concentration of 1.6 wt % methacrylic acid and a mole product of 0.0024. The changes in lens diameter and strain provide additional confirmation of trends observed in the modulus.

FIG. 1 clearly shows the relationship between hydrolytic stability of lenses, and the mole product of anionic group (carboxylate) and TMS silicon content. Only moles of silicon (Si) derived from trimethylsilyl-containing monomers (TRIS or SIMAA2) were used in the calculation of the mole product listed in Tables 2 and 3. From these experiments it was surprisingly found that the stability of silicone hydrogel lenses comprising a silicone component having at least one TMS group and at least one anionic component, such as methacrylic acid, display a sharp drop in stability above a certain concentration of the anionic component. Thus, Examples 1 and 2 have substantially similar stability even though the Example 1 contains twice as much methacrylic acid (1%) than Example 2 (0.5%). However, the stability of the lenses made in Example 3 were much worse than Examples 2 and 3. This result was unexpected, and provides a small formulating window for including anionic components and silicone components comprising at least one TMS group. The inclusion of TMS containing silicone monomer components in amounts that provide the recited stability products provides the ability to balance stability with other properties, such as a desired modulus, elongation or tan delta. The stability products, methacrylic acid concentrations and % change in modulus are shown in Table 8, below.

Comparative Example 1

The reactive monomer mixture listed in Table 1 under CE 1 was dosed into Zeonor front curves, and the molds were closed using Zeonor back curves. The lenses were cured under visible light in a nitrogen atmosphere. Cure profile: 1) Pre-cure (TLDK-30 W/03 bulbs, 30-120 sec, 60-80° C.); 2) Cure (TLD-30 W/03 bulbs, 320-800 sec, 70-80° C.). The molds were opened, and the lenses released were extracted and hydrated in IPA/water mixtures. The finished lenses were packaged in borate buffered saline.

Example 5

A monomer mixture was formed by mixing the components in the amounts listed in Table 4. The monomer mixes were dispensed into Zeonor front and Zeonor:Polypropylene (55:45) back curves. The molds were closed and the filled, closed monomers were held at 65° C. with no irradiation. The monomer mixtures were cured under visible light (Philips TL-03 bulbs) at 65° C. in a nitrogen atmosphere (about 3% $O_2$) using the following cure profile: 1.5 mW/cm² for about 330 seconds, 7±01 mW/cm² for about 440 seconds.

After curing, the molds were opened, and the lenses released in 70% IPA in DI water. After about 60-70 minutes the lenses were transferred into: i) 70% IPA in DI water for about 30-40 minutes; ii) 70% IPA in DI water for about 30-40 minutes; and iii) DI water for at least about 30 minutes.

The lenses were packaged in 950+/−50 uL of borate buffered sodium sulfate solution with 50 ppm methyl cellulose (SSPS) using polypropylene bowls and foil, and autoclaved once (124° C., 18 minutes).

TABLE 4

| Component | Wt % |
|---|---|
| HO-mPDMS 1000 | 55 |
| DMA | 13.53 |
| HEMA | 12.5 |
| TEGDMA | 3 |
| MAA | 1.5 |
| Norbloc | 2.2 |
| PVP 360,000 | 12 |
| Blue HEMA | 0.02 |
| CGI 819 | 0.25 |
| Sum of monomers | 100 |
| Diluent (TPME): | 45 |

The lenses were placed in a chamber with the temperature controlled at 55° C. Lenses were pulled from the chamber at 5, 10 weeks, and tested for modulus, maximum strain, diameter and % water. The results are shown in Table 5.

TABLE 5

| | Example 5, 100% TPME | | |
|---|---|---|---|
| Properties | Baseline | 5 weeks | 10 weeks |
| Modulus (psi) | 93 ± 10 | 105 ± 8 | 102 ± 13 |
| Elongation (%) | 231 ± 61 | 206 ± 43 | 196 ± 39 |
| Gravimetric H$_2$O (%) | 52.2 ± 0.2 | 52.2 ± 0.1 | 52.5 ± 0 |

Examples 6 and 7

Figure 3:
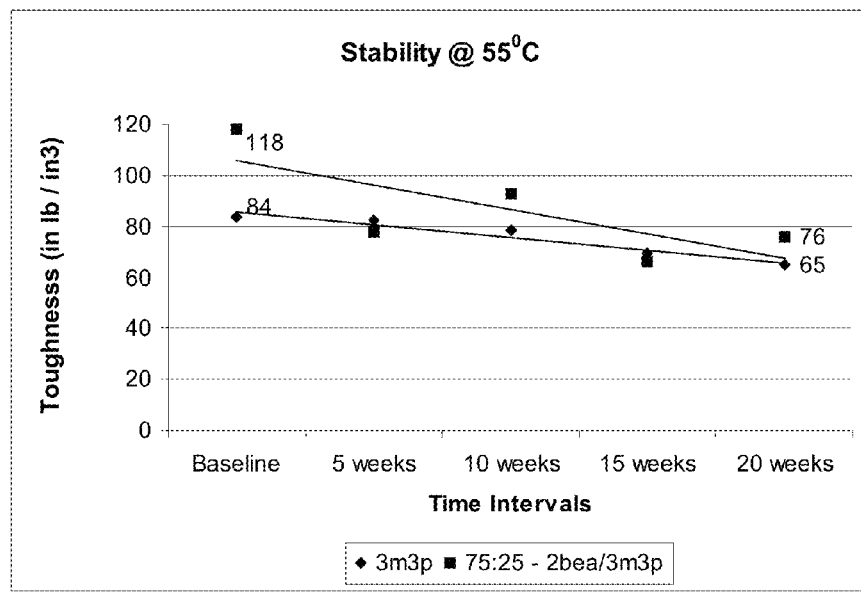
Figure 4:
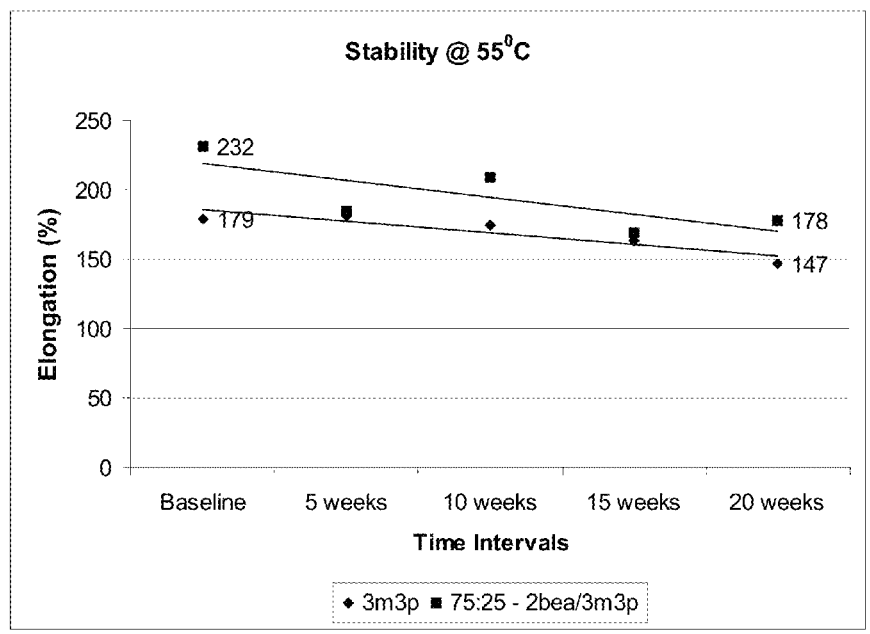

Example 5 was repeated, except that the diluent was changed to those shown in Tables 6-7 below. The lenses were placed in a chamber with the temperature controlled at 55° C. Lenses were pulled from the chamber at 5, 10, 15 and 20 weeks, and tested for modulus, maximum strain and diameter, % water. The stability data from Examples 6-7 is shown in FIGS. 3 and 4.

TABLE 6

| | Example 6, 100% 3-methyl-3-pentanol | | | | |
|---|---|---|---|---|---|
| | Baseline | 5 weeks | 10 weeks | 15 weeks | 20 weeks |
| Modulus (psi) | 98 | 85 | 86 | 87 | 94 |
| Elongation (%) | 179 | 182 | 174 | 163 | 147 |
| Gravimetric H$_2$O (%) | 53.1 | 54.6 | 53.5 | 53.9 | 54.0 |
| Diameter (mm) (−6.00 lens) | 12.62 | 12.44 | 12.42 | 12.45 | 12.50 |

TABLE 7

| | Example 7, 75% butoxy ethyl acetate/35% 3-methyl-3-pentanol | | | | |
|---|---|---|---|---|---|
| Properties | Baseline | 5 weeks | 10 weeks | 15 weeks | 20 weeks |
| Modulus (psi) | 84 | 83 | 71 | 75 | 83 |
| Elongation (%) | 232 | 184 | 209 | 169 | 178 |
| Gravimetric H$_2$O (%) | 53.3 | 54.2 | 53.7 | 53.8 | 54.1 |

TABLE 7-continued

| | Example 7, 75% butoxy ethyl acetate/35% 3-methyl-3-pentanol | | | | |
|---|---|---|---|---|---|
| Properties | Baseline | 5 weeks | 10 weeks | 15 weeks | 20 weeks |
| Diameter (mm) (−1.00 lens) | 14.43 | 14.48 | 14.50 | 14.48 | 14.46 |

The stability product, weight % methacrylic acid and percent change in modulus for each of the Examples is shown in Table 8, below.

TABLE 8

| Ex # | Stability Product | [MAA] (wt %) | [MAA]* | Δ modulus @ 10 wk (%) | Δ modulus @ 18 wk (%) |
|---|---|---|---|---|---|
| 1 | 0.0017 | 1 | 0.012 | 14 | 44 |
| 2 | 0.0008 | 0.5 | 0.006 | NM | 46 |
| 3 | 0.0026 | 1.6 | 0.019 | 35 | 141 |
| 4 | 0.00019 | 1 | 0.006 | 13* | NM |
| CE1 | 0 | 0 | 0 | 12* | NM |
| 5 | 0 | 1.5 | 0.017 | 9.7 | NM |
| 6 | 0 | 1.5 | 0.017 | −12 | −4** |
| 7 | 0 | 1.5 | 0.017 | −15 | −1** |

*measurements taken at 8 weeks
**measurements taken at 20 weeks.

The modulus change noted for Comparative Example 1 illustrates that modulus can vary by as much as 10% without an anionic component. This is also shown by the standard deviations noted in Tables 2 and 3. The change in modulus reported for Examples 6 and 7 are reported as negative values because the modulus was slightly lower after 10 and 20 weeks. However, the changes are within the standard deviation for the modulus test method, and should be considered as representing no change. Table 8 also shows that the best results were achieved in formulations which did not have any silicone monomers having TMS group(s) as a component in the reaction mixture (Example 4, which had mPDMS and macromer, and Examples 5-7 which had HO-mPDMS). The Examples which had PDMS-type silicone as the only silicone (Examples 5-7) displayed the best stability.

Example 8

To a stirred solution of 45.5 kg of 3-allyloxy-2-hydroxypropane methacrylate (AHM) and 3.4 g of butylated hydroxy toluene (BHT) was added 10 ml of Pt (0) divinyltetramethyldisiloxane solution in xylenes (2.25% Pt concentration) followed by addition of 44.9 kg of n-butylpolydimethylsilane. The reaction exotherm was controlled to maintain reaction temperature of about 20° C. After complete consumption of n-butylpolydimethylsilane, the Pt catalyst was deactivated by addition of 6.9 g of diethylethylenediamine. The crude reaction mixture was extracted several times with 181 kg of ethylene glycol until residual AHM content of the raffinate was <0.1%. 10 g of BHT was added to the resulting raffinate, stirred until dissolution, followed by removal of residual ethylene glycol affording 64.5 kg of the OH-mPDMS. 6.45 g of 4-Methoxy phenol (MeHQ) was added to the resulting liquid, stirred, and filtered yielding 64.39 kg of final OH-mPDMS as colorless oil.

Example 9 and Comparative Example 2

The components listed in Table 9, (except PVP K90) were mixed in a jar for at least 1 hour with stirring. The PVP K90 was slowly added to the reactive mixture with stirring such that no clumps were formed during the addition. After all the PVP had been added the reactive mixture was stirred for an additional 30 minutes. The jar was sealed and put on a jar roller running at ~200 rpm over night.

The reactive mixture was degassed in a vacuum desiccator (around 1 cm Hg pressure) for about 40 minutes. The plastic lens molds and monomer dosing syringes were put in a $N_2$ environment (<2% O2) for at least 12 hours. The back curve mold was made of 9544 polypropylene, and the front curve mold was made of Zeonor™. The reactive mixture (50 microliter) was dosed into each FC curve, and then BC curve was slowly deposited to close the molds. This process was carried out under N2 environment (<2% $O_2$).

The monomer mixtures were cured under visible light (Philips TLK 40 W/03 bulbs) in a nitrogen atmosphere (about <2% $O_2$) using the following cure profile: 5±0.5 mW/cm² for about 10 minutes at about 50±5° C.

The base curve was the removed from the assembly by prying. The lens remained with the front curve and the front curve was press-inverted to separate the dry lens from the front curve.

The dry lenses were inspected. Passed lenses were packaged in blister with 950 ul borate buffered packing solution with 50 ppm methyl ethyl cellulose for each lens. The lens was then sterilized at 121° C. for 18 minutes

TABLE 9

| Component | Wt % | |
|---|---|---|
| | Ex. 9 | CE 2 |
| HO-mPDMS | 55 | 55 |
| TEGDMA | 0.25 | 0.25 |
| DMA | 16.78 | 18.28 |
| HEMA | 12.5 | 12.5 |
| MAA | 1.5 | 0 |
| PVP K-90 | 12 | 12 |
| CGI 819 | 0.25 | 0.25 |
| Norbloc | 1.7 | 1.7 |
| Blue HEMA | 0.02 | 0.02 |

Lysozyme and lipocalin uptake were measured as described above.

Lysozyme is a hydrolytic enzyme able to cleave the cell wall of gram positive and some gram negative bacteria. Cleavage of the peptidoglycan wall at the β1-4 linkage between N-acetyl-glucosamine and N acetyl galactosamine (muramate) results in lysis of the bacteria.

Lysozyme activity was measured to determine the capacity of lenses to maintain this protein in its native state. The level of native lysozyme corresponds to the level of active lysozyme determined following the procedure described above. The results are shown in Table 10.

TABLE 10

| Ex. # | [ion] wt % | [ion]* | Lysozyme (μg) | Lipocalin (μg) | % Native lysozyme | PQ1 uptake |
|---|---|---|---|---|---|---|
| 9 | 1.5 | 0.017 | 103 + 5 | 4.6 ± 0.4 | 60 ± 7.7 | 90 |
| CE 2 | 0 | 0 | 6.6 ± 0.3 | 6.5 ± 0.6 | 30 ± 3 | 6 |
| Balafilcon A | 1 | 0.006 | 46 ± 6 | 7.8 ± 0.5 | 37 ± 8.3 | 6 |
| Etafilcon A | 1.98 | 0.023 | 843 ± 23 | 1.8 ± 0.2 | 80 ± 11 | 2 |

*Moles/100 gram of reactive components
Balafilcon A is the lens material used to make Purevision ® lenses commercially available from Bausch & Lomb
Etafilcon A is the lens material used to make ACUVUE ® AND ACUVUE ®2 lenses commercially available from Johnson & Johnson Vision Care, Inc.

Preservatives uptake from lens care solutions can impact contact lens performance, particularly contact lens induced corneal staining Preservative uptake of the lenses of Example 9, Comparative Example 2, and Purevision was measured by incubating the above lenses in 3 ml of OptiFree® RepleniSH® for 72 hours at room temperature using the procedure described above to lysozyme and lipocalin uptake. OptiFree® RepleniSH® contains 0.001 wt % PQ1 as a disinfectant/preservative and citrate dihydrate and citric acid monohydrate concentrations are 0.56% and 0.021% (wt/wt). The quantity of PQ1 uptake was determined using HPLC analysis by comparing the level of PQ1 in the initial soak solution to the level of PQ1 after 72 h soak in presence of the test contact lens. The results are shown in Table 10.

Examples 10-18 & Comparative Example 2

Formulations were made as in Example 9, but varying the concentration of methacrylic acid as shown in Table 11, below. The lysozyme and PQ1 uptake were measured as in Example 9, and the results are shown in Table 12, below. The results are also shown graphically in FIG. 1.

TABLE 9

| Component | Wt % | | | | | | | | | |
|---|---|---|---|---|---|---|---|---|---|---|
| | CE2 | Ex10 | Ex11 | Ex12 | Ex13 | Ex 14 | Ex15 | Ex16 | Ex17 | Ex18 |
| HO-mPDMS | 55 | 55 | 55 | 55 | 55 | 55 | 55 | 55 | 55 | 55 |
| TEGDMA | 0.25 | 0.25 | 0.25 | 0.25 | 0.25 | 0.25 | 0.25 | 0.25 | 0.25 | 0.25 |
| DMA | 18.28 | 18.08 | 17.88 | 17.68 | 17.48 | 17.28 | 17.08 | 16.88 | 16.78 | 16.68 |
| HEMA | 12.5 | 12.5 | 12.5 | 12.5 | 12.5 | 12.5 | 12.5 | 12.5 | 12.5 | 12.5 |
| MAA | 0 | 0.2 | 0.4 | 0.6 | 0.8 | 1.0 | 1.2 | 1.4 | 1.5 | 1.6 |
| PVP K-90 | 12 | 12 | 12 | 12 | 12 | 12 | 12 | 12 | 12 | 12 |
| CGI 819 | 0.25 | 0.25 | 0.25 | 0.25 | 0.25 | 0.25 | 0.25 | 0.25 | 0.25 | 0.25 |
| Norbloc | 1.7 | 1.7 | 1.7 | 1.7 | 1.7 | 1.7 | 1.7 | 1.7 | 1.7 | 1.7 |
| Blue HEMA | 0.02 | 0.02 | 0.02 | 0.02 | 0.02 | 0.02 | 0.02 | 0.02 | 0.02 | 0.02 |

TABLE 10

| Ex # | MAA wt % | [MAA]* | PQ1 (%) per lens | Lysozyme (mg/lens) |
|---|---|---|---|---|
| CE2 | 0 | 0 | 0 (0) | 6.78 (0.48) |
| 10 | 0.2 | 0.002 | 0.0 | 14.23 (1.7) |
| 11 | 0.4 | 0.004 | 2.05 (2.0) | 21.23 (2.31) |
| 12 | 0.6 | 0.007 | 0.36 (0.5) | 37.76 (3.51) |
| 13 | 0.8 | 0.009 | 0.0 | 38.41 (2.93) |
| 14 | 1 | 0.012 | 12.92 (4.4) | 56.55 (10.39) |

TABLE 10-continued

| Ex # | MAA wt % | [MAA]* | PQ1 (%) per lens | Lysozyme (mg/lens) |
|---|---|---|---|---|
| 15 | 1.2 | 0.014 | 42.7 | |
| 16 | 1.4 | 0.016 | 51.5 | |
| 17 | 1.5 | 0.017 | 84.5 (7.8) | 83 (7.21) |
| 18 | 1.6 | 0.019 | 72.6 | |

*Moles/100 gram of reactive components

Figure 5:
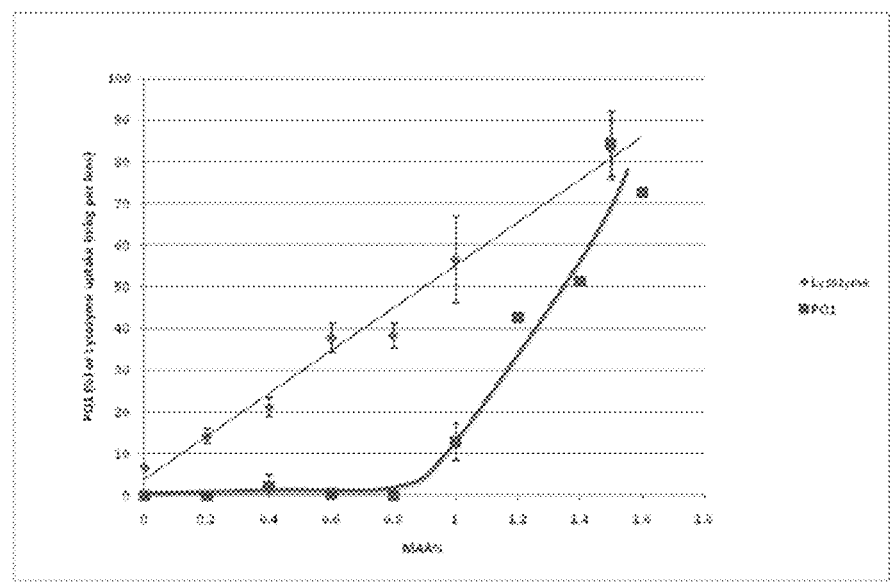
FIG. 5 is graph showing the concentrations of PQ-1 and lysozyme uptaken in the polymer formed in Examples 10-18 and Comparative Example 2.

As is seen in FIG. 5, formulations can be made which display desirable lysozyme uptake, and low PQ1 uptake with existing contact lens care solutions. Thus ophthalmic devices of the present invention display a balance of desirable protein uptake, compatibility with existing lens care solutions and thermal stability.

Examples 19-21 and Comparative Examples 3 & 4

Lenses of Examples 19-21 were made from the formulations listed in Table 11, using the following process.

A monomer mixture was formed by mixing the components in the amounts listed in Table 10. The monomer mixes were dispensed into Zeonor front and Zeonor back curves. The molds were closed and the monomer was cured for about 15 minutes, under visible light (Philips TL-03 bulbs, 1.5 mW/cm$^2$) at ~60° C. in a nitrogen atmosphere (about 0.5% O2).

After curing, the molds were opened, and the lenses released in 70% IPA in DI water. After about 90 minutes the lenses were transferred into: i) 70% IPA in DI water for about 90 minutes and then ii) DI water for at least about 90 minutes.

The lenses were packaged in 950+/−50 uL of borate buffered sodium sulfate solution with 50 ppm methyl cellulose using polypropylene bowls and foil, and autoclaved once (124° C., 18 minutes).

Lenses of Comparative Example 3 were made using the following process. The monomer mix was dispensed into 90/10 Zeonor:Tuftec Blend front and Zeonor back curves. The molds were closed and the monomer was cured under visible light (Philips TLDK 30 w/13) at ~60-65° C. in a nitrogen atmosphere (<3.0% O2) using the following cure profile: 1.0-2.5 mW/cm$^2$ for 240 seconds followed by 4.5-6.5 mW/cm$^2$ for 240 seconds.

After curing, the molds were opened, and the lenses released in 0.45 wt. % sodium borate and deionized water solution. After about 14 minutes the lenses were packaged in 950+/−50 uL of borate buffered sodium sulfate solution with 50 ppm methyl cellulose using polypropylene bowls and foil, and autoclaved once (124° C., 18 minutes).

TABLE 11

| Component | Ex. 19 (wt. %) | Ex. 20 (wt. %) | Ex. 21 (wt. %) | CE3 (wt. %) |
|---|---|---|---|---|
| mPDMS 1000 | 29 | 29 | 29 | 0 |
| HO-mPDMS | 26 | 26 | 26 | 41.5 |
| OH mPDMS dimethacrylate | 1 | 1 | 1 | 0 |
| TEGDMA | 1.5 | 1.5 | 1.5 | 3 |
| DMA | 24 | 24 | 24 | 18.9 |
| HEMA | 9.24 | 8.24 | 7.74 | 22.13 |
| PVP K-90 | 7 | 7 | 7 | 12 |
| Irgacure 819 | 0.24 | 0.24 | 0.24 | 0.25 |
| Norbloc | 2 | 2 | 2 | 2.2 |
| Blue HEMA | 0.02 | 0.02 | 0.02 | 0.02 |
| MAA | 0 | 1 | 1.5 | 0 |
| Monomers % | 77 | 77 | 77 | 55 |
| Decanoic Acid | 60 | 60 | 60 | 60 |
| t-amyl alcohol | 40 | 40 | 40 | 40 |
| Diluents % | 23 | 23 | 23 | 45 |

Comparative Examples 4-6

Poly(HEMA) based lenses with varying amounts of methacrylic acid were made from the formulations listed in Table 12, using boric acid glycerol ester as diluent.

TABLE 12

| Components | Target (%) | | |
|---|---|---|---|
| | CE4 | CE5 | CE6 |
| HEMA | 97.72% | 95.72% | 93.72% |
| MAA | 0.00% | 2.00% | 4.00% |
| EGDMA | 0.78% | 0.78% | 0.78% |
| Irgacure 1700 | 0.45% | 0.45% | 0.45% |
| TMPTMA | 0.10% | 0.10% | 0.10% |
| Norbloc | 0.95% | 0.95% | 0.95% |
| M:D Ratio | 40:60 | 50:50 | 60:40 |

The monomer mixes were dispensed into Zeonor front curves and polypropylene back curves. The molds were closed and the monomer was cured for about 15 minutes, under visible light (Philips TL-03 bulbs, 2 mW/cm$^2$) at ~55° C. in a nitrogen atmosphere (<about 2% O$_2$).

After curing, the molds were opened, and the lenses released in DI water overnight at room temperature.

The lenses were packaged in 950+/−50 uL of borate buffered sodium sulfate solution with 50 ppm methyl cellulose using polypropylene bowls and foil, and autoclaved once (124° C., 18 minutes).

Preparation of Ophthalmic Devices (25 μg and 75 μg of Ketotifen Fumarate)

To prepare 1000 g of a 10 μg/mL ketotifen fumarate ("K-25"):
1. 9.10 g of boric acid
2. 1.00 g of sodium borate decahydrate
3. 8.30 g of sodium chloride
4. 0.10 g of Ca$_2$DTPA
5. 981.475 g of deionized water
6. 0.025 g of ketotifen fumarate The system was maintained at room temperature throughout the solution making process. Components 1-5 were added and stirred using a magnetic or mechanical stirrer until the solution is homogeneous. Ketotifen fumarate was added last and the mixture was stirred to make the solution homogeneous (about 30 minutes).

The procedure to prepare a 75 μg/mL ketotifen fumarate solution was identical to that described above, with the only exceptions being the amount of ketotifen fumarate (0.075 g instead of 0.025 g) and water (981.425 g instead of 981.475 g).

Lenses of Examples 19-21, Comparative Example 3 and 1-Day Acuvue® Brand Contact Lenses (etafilcon A) (each −1.00 D power, except Example 21, which was −0.50 D) were removed from their packages and repackaged in glass vials containing 3.0 mL of the 25 µg/mL or the 75 µg/mL ketotifen fumarate solutions described above to produce K-25 and K-75 lenses, respectively. The vials were sealed with PTFE coated rubber stoppers and heated for 18 minutes at 124° C.

Extraction/Assay Procedure

Drug uptake in each of the lenses was measured as follows. Lenses were removed from their containers using tweezers, blotted and transferred to scintillation vials (one lens/vial).

Three mL of Eluent A (17% acetonitrile in 0.025 postassium phosphate, monobasic buffer 0.2% triethylamine, 0.13% o-phosphoric acid (balance deionized water)) were added to the vials and the vials were sonicated for 1 hour at 35 C. The lenses were removed from the scintillation vials and the remaining solution was analyzed for ketotifen content by HPLC.

Eluent B (50% acetonitrile in 0.025 postassium phosphate, monobasic buffer 0.2% triethylamine, 0.13% o-phosphoric acid (balance deionized water)) was used as the mobile phase, and ketotifen fumarate stock standard 72.72% ketotifen (balance Eluent A).

The HPLC used an Agilent Zorbax Exlipse WDB-18 Rapid Resolution HT 4.6 mm×1.8µ Guard Column: Phenomenex HPLC Guard Cartridge System "Security Guard" and the detector has a wavelength of 299 nm, a VW detector peak width Setting:">0.05 min", a Flow rate of 1.0 mL/min, and an injection volume of 100 µL. The number of micrograms of ketotifen per lens was analyzed by comparing the peak area of the extracted solutions versus peak area of against peak areas of the ketotifen fumarate stock standard and using standard equations. Drug uptake, the partition ratio and diameter is shown in Table 13, below.

The diameter and water content were measured on lenses prior to soaking in the drug solution.

The Partition ratio was calculated based on experimental data:

Drug uptake by lens/(drug uptake by lens+amount drug in pkg. soln.)

The lenses of the present invention display surprisingly improved drug uptake compared to uncharged silicone hydrogel lenses (nearly four-fold increase in uptake between Example 21 to 19) and to anionic conventional lenses, such as etafilcon A, (Example 21 to Comparative Example 5). This is illustrated by the increase in % uptake/[MAA], which was calculated using the following equation:

$$[(\text{Ketotifen uptake}_{ionic\ lens}/\text{Ketotifen uptake}_{non\text{-}ionic\ lens})/[\text{MAA}]_{ionic\ lens}] \times 100$$

So, for Example 20 (59.1/18.4)/1=320%.

Thus the data shows that the lenses of present invention (Examples 20 and 21) display substantially higher percent drug uptake (321 and 257%, respectively) for a given concentration of anionic component than conventional ionic lenses, 98 and 56.3% for Comparative Examples 5 and 6, respectively. Moreover, since the percentages are calculated against a formulation which is the same, except for the iconicity, the difference in ketotifen concentration in the solutions is accounted for.

Drug Release

Figure 6:
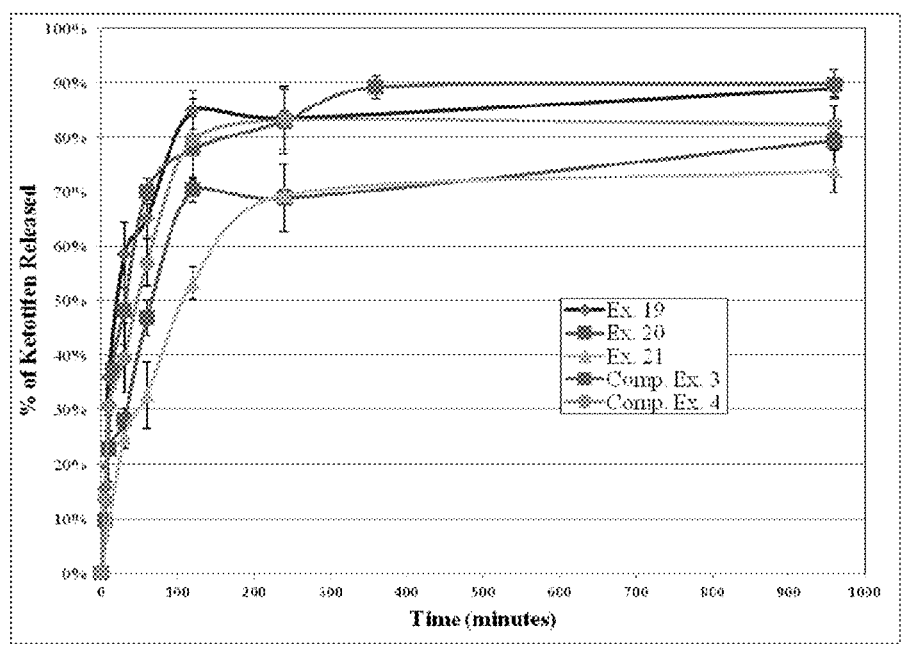
FIG. 6 is a graph showing the release of ketotifen fumarate from the lenses of Examples 19-12 and Comparative Examples 3 and 4.

Lenses were removed from their respective containers, blotted, and transferred to scintillation vials (one lens/vial). Five (5) mL of packing solution was added to each vial and the vials were shaken at 35 C. The solutions for 5 lenses of each of Examples 19-20, and six (6) lenses for the Comparative Examples were analyzed at 5, 30, 60, 120, 240 and 960 minutes for ketotifen content by the extraction/assay procedure above. For Example 21, the solution for 5 lenses were analyzed at 30, 60, 120, 240 and 960 minutes. The amount of ketotifen released by each lens type at each time point is listed in Table 13 below, and shown in FIG. 6.

TABLE 13

| Ex. # | [KF] (µg/mL) | MAA (wt %) | Ketotifen In PS (µg) | Ketotifen Uptake (µg) | Uptake inc./[MAA] | Partition Ratio | Diameter (mm) | [H$_2$O] (%) |
|---|---|---|---|---|---|---|---|---|
| 19 | 75 | 0 | 45.0 (0.24) | 18.4 (0.11) | NA | 0.12 (0.0009) | 14.09 | 38.76 |
| 20 | 75 | 1 | 31.7 (0.43) | 59.1 (0.51) | 321 | 0.383 (0.005) | 13.92 | 44.53 |
| 21 | 75 | 1.5 | 27.5 (0.57) | 70.842 (1.75) | 257 | 0.462 (0.011) | 13.90 | 48.50 |
| CE4 | 25 | 0 | 13.2 (0.18) | 12.40 (0.81) | NA | 0.239 (0.016) | 13.04 | 47.00 |
| CE5 | 25 | 2 | 3.16 (0.24) | 24.31 (0.91) | 98 | 0.470 (0.015) | 15.80 | 61.22 |
| CE6 | 25 | 4 | 7.95 (0.54) | 27.86 (1.68) | 56.2 | 0.539 (0.032) | N.M. | 73.90 |
| CE3 | 75 | 0 | 46.2 (0.41) | 22.8098 (0.49) | NA | 0.141 (0.003) | 14.20 | 48 |

TABLE 13

| Ex# | 0 min | 5 min | 10 min | 30 min | 60 min | 120 min | 240 min | 960 min |
|---|---|---|---|---|---|---|---|---|
| | | | | % Ketotifen Release | | | | |
| 19 | 0 | 15.6 ± 3.6 | 35.8 ± 1.8 | 58.4 ± 6 | 65.2 ± 3.3 | 85 ± 3.5 | 83.5 ± 5.9 | 88.9 ± 1.5 |
| 20 | 0 | 9.6 ± 2.8 | 22.8 ± 6.2 | 28.2 ± 2 | 46.8 ± 3.3 | 70.4 ± 2.3 | 68.8 ± 6.1 | 79.4 ± 1.4 |
| 21 | 0 | NM | NM | 24.9 ± 2 | 32.7 ± 6 | 53.2 ± 3 | 69.4 ± 1 | 73.8 ± 3.8 |
| CE3 | 0 | 37.4 ± 3.5 | 48.3 ± 6.5 | 70.1 ± 2.4 | 77.8 ± 5.9 | 82.9 ± 6 | 89.2 ± 2.1 | 89.8 ± 2.8 |
| CE4 | 0 | 13.6 ± 6.0 | 30.7 ± 4.7 | 39.5 ± 6.3 | 57.0 ± 4.3 | 79.7 ± 7.3 | 83.2 ± 1.5 | 82.4 ± 3.4 |

The modulus and water content of the lenses (−1.00 D) of Examples 12-21 were measured after one and three autoclave cycles. The results are reported in Table 14, below.

| Ex# | [MAA] | AC | Mod. (psi) | [H₂O] |
|---|---|---|---|---|
| 19 | 0 | 1 | 101 | 39 |
| 19 | 0 | 3 | 113 | 40 |
| 20 | 1 | 1 | 120 | 46 |
| 20 | 1 | 3 | 116 | 46 |
| 21 | 1.5 | 1 | 112 | 48 |
| 21 | 1.5 | 3 | 106 | 48 |

Both water content and modulus remained stable through 3 autoclave cycles.

The lenses of Examples 19-21 were autoclaving (121° C. for 21 minutes) three times, and then evaluated for thermal stability using the following conditions:

25° C.±2° C., with ambient humidity ranging from 17% to 56% RH.

The samples were stored in the stability chambers in blisters without being cartoned. Originally, the blisters were placed on their side, to expose the solution to all parts of the container. The blister orientation was changed to horizontal, foil side up ~10 months into the study.

The modulus and water content were tested for the −1.00 lenses, stored at room temperature (25° C.±2° C.) at intervals of 0 (baseline), 1.5, 6, 12 and 18 months. The results are shown in Table 14, below.

TABLE 14

| Ex. # | T (mo) | −1.00 | |
|---|---|---|---|
| | | [H₂O] (%) | Mod (psi) |
| 19 | 0 | 40 | 113 |
| 0% | 1.5 | 40 | 125 |
| | 6 | 40 | 138 |
| | 12 | 40 | 114 |
| | 18 | 40* | 110 |
| 20 | 0 | 46 | 116 |
| 1.0% | 1.5 | 46 | 129 |
| | 6 | 46 | 132 |
| | 12 | 47 | 110 |
| | 18 | 47 | 115 |
| 21 | 0 | 48 | 106 |
| 1.5% | 1.5 | 49 | 130 |
| | 6 | 49 | 131 |
| | 12 | 49 | 108 |
| | 18 | 49 | 113 |

*water content for the last data point of Example 19% was measured at 21 months.

We claim:

1. A contact lens formed from reactive components comprising about 0.1 to about 10 mmol/100 gm reactive mixture of at least one anionic component comprising at least one carboxylic acid group and at least one silicone component selected from the group consisting of reactive polydialkylsiloxane selected from compounds of Formula I:

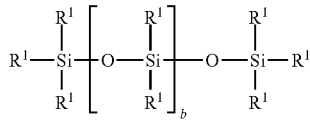

where b=2 to 20; one terminal $R^1$ comprises an ethylenically unsaturated moiety, at least one $R^1$ on a terminal silicone not substituted with an ethylenically unsaturated moiety is independently selected from monovalent groups comprising, monovalent alkyl group having 2 to 16 carbon atoms, and the remaining $R^1$ are selected from monovalent alkyl groups having 1 to 16 carbon atoms, wherein said reactive components comprise less than 5 wt % TRIS, are free of linear polysiloxane crosslinkers and wherein said contact lens further comprises at least one pharmaceutical or neutraceutical component.

2. The contact lens of claim 1 wherein said reactive components are free of TRIS.

3. The contact lens of claim 2 wherein said ionic component comprises at least one polymerizable group and three to ten carbon atoms.

4. The contact lens of claim 2 where said ionic component comprises three to eight carbon atoms.

5. The contact lens of claim 1 wherein said ionic component is a carboxylic acid containing component selected from the group consisting of free radical reactive carboxylic acids comprising 1-8 carbon atoms.

6. The contact lens of claim 1 wherein said ionic component comprises at least one carboxylic acid group.

7. The contact lens of claim 1 wherein said carboxylic acid-containing component is selected from the group consisting of (meth)acrylic acid, acrylic acid, itaconic acid, crotonic acid, cinnamic acid, vinylbenzoic acid, fumaric acid, maleic acid, N-vinyloxycarbonyl alanine, 3-acrylamidopropionic acid, 4-acrylamidobutanoic acid, 5-acrylamidopentanoic acid, N-vinyloxycarbonyl-α-alanine, N-vinyloxycarbonyl-β-alanine (VINAL), 2-vinyl-4,4-dimethyl-2-oxazolin-5-one (VDMO), reactive sulphonate salts, including sodium-2-(acrylamido)-2-methylpropane sulphonate, 3-sulphopropyl (meth)acrylate potassium salt, 3-sulphopropyl (meth)acrylate sodium salt, bis 3-sulphopropyl itaconate di sodium, bis 3-sulphopropyl itaconate di potassium, vinyl sulphonate sodium salt, vinyl sulphonate salt, styrene sulphonate, 2-sulphoethyl methacrylate and mixtures thereof.

8. The contact lens of claim 1 wherein said carboxylic acid-containing component comprises methacrylic acid, 3-acrylamidopropionic acid, 4-acrylamidobutanoic acid, 5-acrylamidopentanoic acid, N-vinyloxycarbonyl-α-alanine, N-vinyloxycarbonyl-β-alanine (VINAL), and mixtures thereof.

9. The contact lens of claim 8 wherein said carboxylic acid-containing component comprises methacrylic acid.

10. The contact lens of claim 1 wherein said at least one silicone component is selected from the group consisting of mono(meth)acryloxypropyl terminated mono-n-$C_{1-4}$alkyl terminated polydialkylsiloxane, (meth)acryloxypropyl-terminated polydialkylsiloxane, mono-(3-methacryloxy-2-hydroxypropyloxy)propyl terminated, mono-$C_{1-4}$alkyl alkyl terminated polydialkylsiloxane and combinations thereof.

11. The contact lens of claim 1 wherein said at least one silicone component is selected from mono(meth)acryloxypropyl terminated mono-n-butyl terminated polydimethylsiloxane, mono(meth)acryloxypropyl terminated polydimethylsiloxane, mono-(3-methacryloxy-2-hydroxypropyloxy) propyl terminated, mono-butyl terminated polydialkylsiloxane mono-(3-methacryloxy-2-hydroxypropyloxy)propyl terminated, mono-methyl terminated polydialkylsiloxane combinations thereof and the like.

12. The contact lens of claim 1 wherein said at least one silicone component is selected from monomethacryloxypropyl-terminated mono-n-butyl terminated polydimethysiloxane, methacryloxypropyl-terminated polydimethylsiloxane and mono-(3-methacryloxy-2-hydroxypropyloxy)propyl terminated, mono-butyl terminated polydimethylsiloxane and mixtures thereof.

13. The contact lens of claim 1 wherein said at least one pharmaceutical or neutraceutical component is cationic.

14. The contact lens of claim 1 wherein said at least one pharmaceutical or neutraceutical component is selected from the group consisting of atropine, pirenzepine, doxycycline, brimonidine, brinzolamide, dorzolamide, betaxolol, apraclonidine, ccr2 antagonist, olopatadine, alcaftadine, betaxolol, bupivacaine, carbachol, carteolol, chlortetracycline, cyclopentolate, dibutoline, dipivefrin, ephedrine, erythromycin, gentamycin, gramicidin, homatropine ketotifen, levobunolol, levocabastine, lidocaine, lignocaine, lomefloxacin, mepivacaine, naphazoline, neomycin, ofloxacin, oxybuprocaine, pheniramine, physostigmine, pilocarpine, polymyxin B, proparacaine, pyrilamine, tetracaine, tetracycline, tetrahydozoline, timolol, tropicamide, vidarabine, pharmaceutically acceptable salts thereof and combinations thereof and the like.

15. The contact lens of claim 1 wherein said at least one pharmaceutical or neutraceutical component is selected from the group consisting of atropine, pirenzepine, doxycycline, brimonidine, brinzolamide, dorzolamide, betaxolol, apraclonidine, ccr2 antagonist, olopatadine, alcaftadine, betaxolol, bupivacaine, carbachol, carteolol, chlortetracycline, cyclopentolate, dibutoline, dipivefrin, erythromycin, gentamycin, gramicidin, homatropine ketotifen, levobunolol, levocabastine, lidocaine, lignocaine, lomefloxacin, mepivacaine, naphazoline, ofloxacin, pheniramine, physostigmine, pilocarpine, polymyxin B, proparacaine, pyrilamine, tetracaine, tetrahydozoline, timolol, tropicamide pharmaceutically acceptable salts thereof and combinations thereof and the like.

16. The contact lens of claim 1 wherein said at least one pharmaceutical or neutraceutical component is selected from the group consisting of atropine, ketotifen, olopatadine, alcaftadine, levocabastine, pirenzepine, doxycycline, brimonidine, brinzolamide, dorzolamide, betaxolol, apraclonidine, ccr2 antagonist, olopatadine pharmaceutically acceptable salts thereof and combinations thereof and the like.

17. The contact lens of claim 1, 14, 15 or 16, wherein said at least one pharmaceutical or neutraceutical component is added in a symptom mitigating effective amount.

18. The contact lens of claims 17 wherein said symptom mitigating effective amount is between about 5 µg and about less than 200 µg.

19. The contact lens of claims 17 wherein said symptom mitigating effective amount is between about 9 µg and about 100 µg.

20. The contact lens of claims 17 wherein said symptom mitigating effective amount alleviates symptoms for between about 5 minutes, and about 12 hours from insertion of said contact lens on a human's eye.

21. The contact lens of claim 1 wherein said contact lens absorbs at least about 50 µg lysozyme.

22. The contact lens of claim 1 wherein said contact lens absorbs at least about 100 µg lysozyme.

23. The contact lens of claim 1 wherein said contact lens absorbs at least about 200 µg lysozyme.

24. The contact lens of claim 1 wherein said contact lens absorbs about 3 µg or less lipocalin.

25. The contact lens of claim 1 wherein at least about 60% of all proteins absorbed in or on said contact lens are in native form.

26. The contact lens of claim 1 wherein at least about 75% of all proteins absorbed in or on said contact lens are in native form.

27. The contact lens of claim 1 further comprising a water content of at least about 15%.

28. The contact lens of claim 1 further comprising a Dk of at least about 50.

29. The contact lens of claim 28 wherein at least about 75% of all proteins absorbed in or on said contact lens are in native form.

* * * * *